United States Patent
Sambelashvili

(10) Patent No.: US 9,511,233 B2
(45) Date of Patent: *Dec. 6, 2016

(54) SYSTEMS AND METHODS FOR LEADLESS CARDIAC RESYNCHRONIZATION THERAPY

(71) Applicant: Medtronic, Inc., Minneapolis, MN (US)

(72) Inventor: Aleksandre T. Sambelashvili, Maple Grove, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/173,328

(22) Filed: Feb. 5, 2014

(65) Prior Publication Data
US 2015/0142070 A1 May 21, 2015

Related U.S. Application Data

(60) Provisional application No. 61/907,040, filed on Nov. 21, 2013.

(51) Int. Cl.
*A61N 1/00* (2006.01)
*A61N 1/368* (2006.01)
(Continued)

(52) U.S. Cl.
CPC ........... *A61N 1/3682* (2013.01); *A61N 1/3688* (2013.01); *A61N 1/3756* (2013.01); *A61N 1/3627* (2013.01);
(Continued)

(58) Field of Classification Search
CPC . A61N 1/368; A61N 1/36585; A61N 1/37247
(Continued)

(56) References Cited

U.S. PATENT DOCUMENTS 4,280,502 A 7/1981 Baker, Jr. et al.
4,374,382 A 2/1983 Markowitz
(Continued)

FOREIGN PATENT DOCUMENTS

EP 0728497 B1 4/2002
EP 1541191 6/2005
(Continued)

OTHER PUBLICATIONS

"Epicardial Wireless Pacemaker for Improved Left Ventricular Resynchronization (Conceptual Design)" by Rodney Hawkins, Dec. 2010, Thesis presented to the Faculty of California Polytechnic State University, San Luis Obispo.
(Continued)

*Primary Examiner* — Edward Moran
*Assistant Examiner* — Nadia A Mahmood
(74) *Attorney, Agent, or Firm* — Carol F. Barry

(57) ABSTRACT

Techniques and systems for monitoring cardiac arrhythmias and delivering electrical stimulation therapy using a subcutaneous device (e.g. subcutaneous implantable (SD)) is described. In one or more other embodiments, SD is implanted into a patient's heart. Electrical signals are then sensed which includes moderately lengthened QRS duration data from the patient's heart. A determination is made as to whether cardiac resynchronization pacing therapy (CRT pacing) is appropriate based upon the moderately lengthened QRS duration in the sensed electrical signals. The CRT pacing pulses are delivered to the heart using electrodes. In one or more embodiments, the SD can switch between fusion pacing and biventricular pacing based upon data (e.g. moderately lengthened QRS, etc.) sensed from the heart.

26 Claims, 11 Drawing Sheets

(51) Int. Cl.
*A61N 1/375* (2006.01)
*A61N 1/365* (2006.01)
*A61N 1/39* (2006.01)
*A61N 1/362* (2006.01)

(52) U.S. Cl.
CPC .......... *A61N 1/3684* (2013.01); *A61N 1/36592* (2013.01); *A61N 1/3962* (2013.01)

(58) Field of Classification Search
USPC ................................................ 607/9, 18, 30
See application file for complete search history.

(56) References Cited

U.S. PATENT DOCUMENTS

| | | | |
|---|---|---|---|
| 4,787,389 A | 11/1988 | Tarjan | |
| 4,830,006 A | 5/1989 | Haluska et al. | |
| 4,865,037 A | 9/1989 | Chin et al. | |
| 5,117,824 A | 6/1992 | Keimel et al. | |
| 5,144,950 A | 9/1992 | Stoop et al. | |
| 5,174,289 A | 12/1992 | Cohen | |
| 5,193,539 A | 3/1993 | Schulman et al. | |
| 5,255,692 A | 10/1993 | Neubauer et al. | |
| 5,318,594 A | 6/1994 | Limousin et al. | |
| 5,683,426 A | 11/1997 | Greenhut et al. | |
| 5,749,909 A | 5/1998 | Schroeppel et al. | |
| 5,814,089 A | 9/1998 | Stokes et al. | |
| 5,817,130 A | 10/1998 | Cox et al. | |
| 5,928,271 A | 7/1999 | Hess et al. | |
| 6,256,534 B1 | 7/2001 | Dahl | |
| 6,393,316 B1 | 5/2002 | Gillberg et al. | |
| 6,442,426 B1 | 8/2002 | Kroll | |
| 6,508,771 B1 | 1/2003 | Padmanabhan et al. | |
| 6,512,940 B1 | 1/2003 | Brabec et al. | |
| 6,522,915 B1 | 2/2003 | Ceballos et al. | |
| 6,526,311 B2 | 2/2003 | Begemann | |
| 6,597,951 B2 | 7/2003 | Kramer et al. | |
| 6,622,046 B2 | 9/2003 | Fraley et al. | |
| 6,721,597 B1 | 4/2004 | Bardy et al. | |
| 6,754,528 B2 | 6/2004 | Bardy et al. | |
| 6,788,971 B1 | 9/2004 | Sloman et al. | |
| 6,871,096 B2 | 3/2005 | Hill | |
| 6,904,315 B2 | 6/2005 | Panken et al. | |
| 6,934,585 B1 | 8/2005 | Schloss et al. | |
| 6,993,389 B2 | 1/2006 | Ding et al. | |
| 7,013,176 B2 | 3/2006 | Ding et al. | |
| 7,181,284 B2 | 2/2007 | Burnes et al. | |
| 7,231,248 B2 | 6/2007 | Kramer et al. | |
| 7,231,253 B2 | 6/2007 | Tidemand et al. | |
| 7,272,448 B1 | 9/2007 | Morgan et al. | |
| 7,346,393 B2 | 3/2008 | Spinelli et al. | |
| 7,558,626 B2 | 7/2009 | Corbucci | |
| 7,610,092 B2 | 10/2009 | Cowan et al. | |
| 7,630,764 B2 | 12/2009 | Ding et al. | |
| 7,634,313 B1 | 12/2009 | Kroll et al. | |
| 7,657,313 B2 | 2/2010 | Rom | |
| 7,706,879 B2 | 4/2010 | Burnes et al. | |
| 7,848,815 B2 | 12/2010 | Brisken et al. | |
| 7,877,144 B2 | 1/2011 | Coles, Jr. et al. | |
| 7,881,791 B2 | 2/2011 | Sambelashvili et al. | |
| 7,890,173 B2 | 2/2011 | Brisken et al. | |
| 7,894,902 B2 | 2/2011 | Rom | |
| 7,912,544 B1 | 3/2011 | Min et al. | |
| 7,930,027 B2 | 4/2011 | Prakash et al. | |
| 7,937,148 B2 | 5/2011 | Jacobson | |
| 7,941,218 B2 | 5/2011 | Sambelashvili et al. | |
| 7,953,493 B2 | 5/2011 | Fowler et al. | |
| 7,991,467 B2 | 8/2011 | Markowitz et al. | |
| 7,996,087 B2 | 8/2011 | Cowan et al. | |
| 8,002,718 B2 | 8/2011 | Buchholtz et al. | |
| 8,032,219 B2 | 10/2011 | Neumann et al. | |
| 8,046,065 B2 | 10/2011 | Burnes et al. | |
| 8,145,308 B2 | 3/2012 | Sambelashvili et al. | |
| 8,204,590 B2 | 6/2012 | Sambelashvili et al. | |
| 8,214,041 B2 | 7/2012 | Van Gelder et al. | |
| 8,315,701 B2 | 11/2012 | Cowan et al. | |
| 8,321,014 B2 | 11/2012 | Maskara et al. | |
| 8,352,027 B2 | 1/2013 | Spinelli et al. | |
| 8,391,964 B2 | 3/2013 | Musley et al. | |
| 8,428,716 B2 | 4/2013 | Mullen et al. | |
| 8,457,742 B2 | 6/2013 | Jacobson | |
| 8,467,871 B2 | 6/2013 | Maskara | |
| 8,521,268 B2 | 8/2013 | Zhang et al. | |
| 8,617,082 B2 | 12/2013 | Zhang et al. | |
| 8,639,333 B2 | 1/2014 | Stadler et al. | |
| 8,676,314 B2 | 3/2014 | Maskara et al. | |
| 8,718,773 B2 | 5/2014 | Willis et al. | |
| 8,744,572 B1 | 6/2014 | Greenhut et al. | |
| 8,768,459 B2 | 7/2014 | Ghosh et al. | |
| 8,886,307 B2 | 11/2014 | Sambelashvili et al. | |
| 8,886,311 B2 | 11/2014 | Anderson et al. | |
| 8,923,963 B2 | 12/2014 | Bonner et al. | |
| 9,008,776 B2 | 4/2015 | Cowan et al. | |
| 2004/0215308 A1 | 10/2004 | Bardy et al. | |
| 2005/0137629 A1* | 6/2005 | Dyjach et al. | ................... 607/9 |
| 2005/0277990 A1 | 12/2005 | Ostroff et al. | |
| 2006/0161205 A1 | 7/2006 | Mitrani et al. | |
| 2006/0235478 A1 | 10/2006 | Van Gelder et al. | |
| 2006/0241705 A1 | 10/2006 | Neumann et al. | |
| 2007/0049975 A1 | 3/2007 | Cates et al. | |
| 2007/0088394 A1 | 4/2007 | Jacobson | |
| 2007/0088398 A1 | 4/2007 | Jacobson | |
| 2007/0293900 A1 | 12/2007 | Sheldon et al. | |
| 2007/0299475 A1 | 12/2007 | Levin et al. | |
| 2008/0154322 A1 | 6/2008 | Jackson et al. | |
| 2008/0269816 A1 | 10/2008 | Prakash et al. | |
| 2008/0269823 A1 | 10/2008 | Burnes et al. | |
| 2009/0036941 A1 | 2/2009 | Corbucci | |
| 2009/0234411 A1 | 9/2009 | Sambelashvili et al. | |
| 2009/0234412 A1 | 9/2009 | Sambelashvili | |
| 2009/0234413 A1* | 9/2009 | Sambelashvili et al. | ....... 607/25 |
| 2009/0234414 A1 | 9/2009 | Sambelashvili et al. | |
| 2009/0234415 A1 | 9/2009 | Sambelashvili et al. | |
| 2009/0248103 A1 | 10/2009 | Sambelashvili et al. | |
| 2009/0275998 A1 | 11/2009 | Burnes et al. | |
| 2010/0016911 A1 | 1/2010 | Willis et al. | |
| 2010/0016914 A1 | 1/2010 | Mullen et al. | |
| 2010/0023078 A1 | 1/2010 | Dong et al. | |
| 2010/0042108 A1 | 2/2010 | Hibino | |
| 2010/0152798 A1 | 6/2010 | Sanghera et al. | |
| 2010/0185250 A1 | 7/2010 | Rom | |
| 2010/0198291 A1 | 8/2010 | Sambelashvili et al. | |
| 2010/0228308 A1 | 9/2010 | Cowan et al. | |
| 2010/0286541 A1 | 11/2010 | Musley et al. | |
| 2011/0071586 A1 | 3/2011 | Jacobson | |
| 2011/0106202 A1 | 5/2011 | Ding et al. | |
| 2011/0190841 A1 | 8/2011 | Sambelashvili et al. | |
| 2011/0196444 A1 | 8/2011 | Prakash et al. | |
| 2012/0035685 A1 | 2/2012 | Saha et al. | |
| 2012/0109235 A1 | 5/2012 | Sheldon et al. | |
| 2012/0109236 A1 | 5/2012 | Jacobson et al. | |
| 2012/0263218 A1 | 10/2012 | Dal Molin et al. | |
| 2012/0296228 A1 | 11/2012 | Zhang et al. | |
| 2012/0316613 A1 | 12/2012 | Keefe et al. | |
| 2013/0013017 A1 | 1/2013 | Mullen et al. | |
| 2013/0053906 A1 | 2/2013 | Ghosh et al. | |
| 2013/0066169 A1 | 3/2013 | Rys et al. | |
| 2013/0116738 A1 | 5/2013 | Samade et al. | |
| 2013/0131750 A1 | 5/2013 | Stadler et al. | |
| 2013/0131751 A1 | 5/2013 | Stadler et al. | |
| 2013/0197599 A1 | 8/2013 | Sambelashvili et al. | |
| 2013/0231710 A1 | 9/2013 | Jacobson | |
| 2013/0268017 A1 | 10/2013 | Zhang et al. | |
| 2013/0274828 A1 | 10/2013 | Willis | |
| 2013/0282073 A1 | 10/2013 | Cowan et al. | |
| 2014/0114372 A1 | 4/2014 | Ghosh et al. | |
| 2014/0330208 A1 | 11/2014 | Christie et al. | |
| 2014/0330326 A1 | 11/2014 | Thompson-Naumann et al. | |
| 2014/0358135 A1 | 12/2014 | Sambelashvili et al. | |

(56) References Cited

U.S. PATENT DOCUMENTS

| | | |
|---|---|---|
| 2015/0142069 A1 | 5/2015 | Sambelashvili |
| 2015/0142070 A1 | 5/2015 | Sambelashvili |
| 2016/0051821 A1 | 2/2016 | Sambelashvili et al. |

FOREIGN PATENT DOCUMENTS

| | | |
|---|---|---|
| EP | 2471452 A1 | 7/2012 |
| EP | 1703944 B1 | 8/2015 |

OTHER PUBLICATIONS

U.S. Appl. No. 14/801,049, filed Jul. 16, 2015.
U.S. Appl. No. 13/665,601 to Bonner et al., entitled, "Leadless Pacemaker System," filed Oct. 31, 2012.
U.S. Appl. No. 14/261,460, filed Apr. 25, 2014, entitled "Implantable Medical Device System Having Implantable Cardiac Defibrillator System and Substernal Leadless Pacing Device".
U.S. Appl. No. 14/257,462, filed Apr. 21, 2014 entitled "Anchoring an Implantable Medical Device Within a Substernal Space".
(PCT/US2014/036782) PCT Notification of Transmittal of the International Search Report and the Written Opinion of the International Searching Authority, Mailed Aug. 22, 2014, 12 pages.
Ganapathy et al., "Implantable Device to Monitor Cardiac Activity with Sternal Wires," Pace, vol. 37, Dec. 2014, 11 pages.
Guenther et al., "Substernal Lead Implantation: A Novel Option to Manage DFT Failure in S-ICD patients," Clinical Research Cardiology, Published On-line Oct. 2, 2014, 3 pages.
Tung et al., "Initial Experience of Minimal Invasive Extra Cardiac Placement of High Voltage Defibrillator Leads," Canadian Cardiovascular Congress 2007, Oct. 2007, vol. 23, Supplement SC, Abstract 0697, http://www.pulsus.com/ccc2007/abs/0697.htm, 2 pages.
(PCT/US2014/066792) PCT Notification of Transmittal of the International Search Report and the Written Opinion of the International Searching Authority.
(PCT/US2013/013601) PCT Notification of Transmittal of the International Search Report and the Written Opinion of the International Searching Authority.
Rodney Hawkins, "Epicardial Wireless Pacemaker for Improved Left Ventricular Reynchronization (Conceptual Design)", Dec. 2010, A Thesis presented to the Faculty of California Polytechnic State University, San Luis Obispo, 57 pp.

* cited by examiner

SYSTEMS AND METHODS FOR LEADLESS CARDIAC RESYNCHRONIZATION THERAPY

RELATED APPLICATION

The present application claims priority and other benefits from U.S. Provisional Patent Application Ser. No. 61/907,040, filed Nov. 21, 2013, entitled "SYSTEMS AND METHODS FOR LEADLESS CARDIAC RESYNCHRONIZATION THERAPY", incorporated herein by reference in its entirety.

CROSS-REFERENCE TO RELATED APPLICATION

Cross-reference is hereby made to the commonly-assigned related U.S. applications, Ser. No. 14/173,288, entitled "SYSTEMS AND METHODS FOR LEADLESS CARDIAC RESYNCHRONIZATION THERAPY", to Sambelashvili, filed concurrently herewith and incorporated herein by reference in their entireties.

TECHNICAL FIELD

The invention relates to medical devices, and, more particularly, to implantable medical devices configured to detect and treat cardiac arrhythmias.

BACKGROUND

Some types of implantable medical devices (IMDs), such as cardiac pacemakers or implantable cardioverter defibrillators (ICDs), provide therapeutic electrical stimulation to a heart of a patient via electrodes on one or more implantable endocardial or epicardial leads that are positioned in or adjacent to the heart. The therapeutic electrical stimulation may be delivered to the heart in the form of pulses or shocks for pacing, cardioversion or defibrillation. In some cases, an IMD may sense intrinsic depolarizations of the heart, and control the delivery of therapeutic stimulation to the heart based on the sensing.

Other types of IMDs include a leadless pacemaker, which may be used to sense electrical activity and/or deliver therapeutic signals to the heart. The leadless pacemaker may include one or more electrodes on its outer housing to deliver therapeutic electrical signals and/or sense intrinsic depolarizations of the heart. The leadless pacemaker may be positioned within or outside of the heart and, in some examples, may be anchored to a wall of the heart via a fixation mechanism.

Delivery of therapeutic electrical stimulation to the heart can be useful in addressing cardiac conditions such as ventricular dyssynchrony that may occur in patients. Ventricular dyssynchrony is a lack of synchrony or a difference in the timing of contractions in different ventricles of the heart. Significant differences in timing of contractions can reduce cardiac efficiency. Cardiac resynchronization therapy (CRT), delivered by an IMD to the heart, may enhance cardiac output by resynchronizing the electromechanical activity of the ventricles of the heart.

It is generally known that a greater number of patients may benefit from CRT but choose to forgo the therapy for a variety of reasons. For example, implanting an IMD involves a long procedure (~1.5-2 hours) requiring skilled electrophysiologists (EPs), who are unavailable in some rural areas. Additionally, although post-implant complications are unlikely, issues can arise such as LV lead dislodgement, phrenic nerve stimulation, and pocket hematomas. Moreover, some patients are non-responsive to CRT which may be due to the location electrical stimulation is delivered. It is therefore desirable to develop new methods and systems for delivering CRT that reduces the likelihood of post-implant complications and may be able to deliver more effective CRT.

SUMMARY

Generally, this disclosure describes various techniques and systems for monitoring cardiac conditions and delivering cardiac resynchronization therapy (CRT) (e.g. fusion pacing etc.) by using a subcutaneous device (SD) (e.g. subcutaneous implantable cardioverter defibrillator (SICD), loop recorder (e.g. REVEAL®), etc.) and/or a leadless pacing device (LPD) such as a percutaneous leadless pacing system. In particular, a conventional left ventricular lead is eliminated through the LPD being placed into a chamber of the heart.

After the SD and the LPD have been implanted, a first electrical signal (also referred to as the baseline rhythm) is sensed from a heart of a patient through the SD. The baseline rhythm can be an intrinsic rhythm of the heart or the rhythm that occurs with right ventricular (RV) pacing only. The first electrical signal is sensed as a subcutaneous ECG. Data extracted from the first signal is stored into memory of the SD. Post-implant, a second signal is sensed from the heart through the SD. Data is extracted from the second signal, which is stored into memory of the SD. A cardiac condition (e.g. ventricular dyssynchrony, etc.) can be determined to be present. After data, extracted from the first electrical signal (i.e. baseline), is compared to data extracted from the second electrical signal (post-implant signal). A determination is made at the time of implant or post-implant as to whether CRT is appropriate to treat the detected cardiac condition. The timing of the pacing pulses can be determined either by the SD or LPD device. Preferably, the SD determines the timing of the pulses. A determination can then be made as to the timing of the delivery of electrical stimuli (e.g. pacing pulses etc.) that is synchronized with the activation of the atria and right ventricle (RV). Electrical stimuli is typically delivered to the left ventricle (LV) but depending upon the patient's condition, electrical stimuli can be optionally delivered to another chamber of the heart such as the right ventricle by another leadless pacing device (LPD) to cardiac tissue. The LPD then receives communication from the SD requesting the LPD to deliver CRT to the heart. The SD senses and extracts data from a third electrical signal from the heart of the patient to determine whether the pacing by LPD provided efficacious resynchronization or whether the delivery and timing of the LPD pulse should be modified.

Another embodiment of the present disclosure is directed to a combination of a LPD and an intravenously implanted device (IID) to deliver CRT using the same or similar technique described above. In particular, the LPD delivers pacing pulses to cardiac tissue after receiving a command signal from the IID.

Yet other embodiments of the present disclosure is directed to an LPD used in combination with an ICD or a pacemaker. In particular, the LPD delivers pacing pulses to cardiac tissue after receiving a command signal from the ICD or pacemaker and terminates CRT when a termination condition is met.

In addition, the SD and the LPD may be configured to engage in one-way or two-way communication between the SD and the LPD. This one-way or two-way communication may be used to initiate therapy and/or confirm that therapy should be delivered. For example, one-way communication may allow the SD to transmit a communication message to the LPD instructing the LPD to deliver CRT. Left-Ventricular (LV) pacing can be achieved using a miniaturized percutaneous leadless pacing system (PLPS) placed on the endocardial wall of the LV or substernally/retrosternally. Such pacing resolves problems associated the conventional devices.

In another embodiment, the SD transmits a control signal to the LPD to initiate CRT. The LPD senses a cardiac signal (i.e. a second electrical signal) from the heart of the patient. Based on the cardiac signal, the LPD could determine whether to deliver CRT or the type of CRT to deliver to the heart from the LPD. In one or more embodiments, the LPD, based on the second electrical signal, could initially determine that CRT is not necessary. The initial determination by the LPD could use very simplified tests such as a threshold of one or more parameters. In one or more embodiments, the SD could perform a more detailed analysis as to whether CRT should be delivered. Using the sensed data from the LPD and/or SD, the SD could generate another signal to the LPD that either confirms or overrides the LPDs initial determination.

In another embodiment, the LPD could sense a cardiac signal that indicates a switch should occur between fusion pacing to biventricular pacing. Determining whether to switch between fusion pacing and biventricular pacing could be determined based upon one or more parameters (e.g. moderately lengthened QRS, etc.). The LPD could be configured to either automatically switch between fusion pacing and biventricular pacing or to wait until the SD confirms or denies switching between the CRT pacing mode (i.e. fusion pacing and biventricular pacing). The SD could be configured to send a confirmatory signal or a signal denying the LPD switching the pacing mode.

In yet another embodiment, the LPD could determine that biventricular pacing is required over fusion pacing in contravention to the SD communication. In one embodiment, the LPD would deliver biventricular pacing. In one or more other embodiments, the LPD could determine that fusion pacing is required over biventricular pacing in contravention to the SD communication. In this scenario, the LPD could deliver fusion pacing.

In one or more other embodiments, SD is implanted into a patient's heart. For example, the SD could be a conventional ICD or a SD described herein). Electrical signals are then sensed which includes moderately lengthened QRS duration data from the patient's heart. A determination is made as to whether cardiac resynchronization pacing therapy (CRT pacing) is appropriate based upon the moderately lengthened QRS duration in the sensed electrical signals. The CRT pacing pulses are delivered to the heart using electrodes. In one or more embodiments, the SD can switch between fusion pacing and biventricular pacing based upon data (e.g. moderately lengthened QRS, etc.) sensed from the heart.

The details of one or more examples are set forth in the accompanying drawings and the description below. Other features, objects, and advantages will be apparent from the description and drawings, and from the claims.

DETAILED DESCRIPTION

Figure 1:
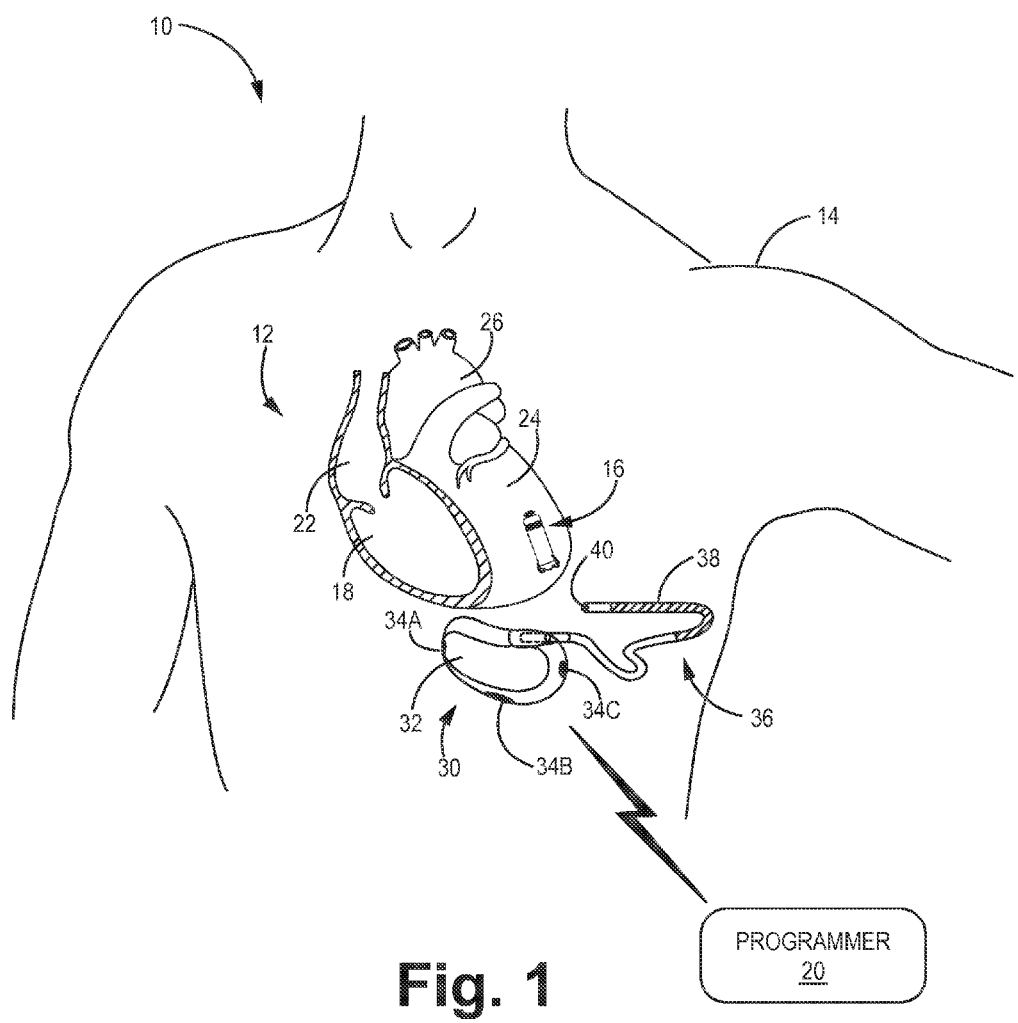
FIG. 1 is a conceptual drawing illustrating an example system that includes a subcutaneous implantable cardioverter defibrillator (SICD) implanted exterior to the rib cage of a patient and a leadless pacing device (LPD) implanted within a cardiac chamber of the patient.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

As described herein, the present disclosure provides many benefits to physicians and patients who receive implantable medical devices for delivery of cardiac resynchronization therapy (CRT). For example, the present disclosure reduces the time spent and expertise needed by a physician to implant a subcutaneous device (e.g. subcutaneous implantable cardioverter defibrillator (SICD), loop recorder (e.g. REVEAL) etc.) and a leadless pacing device (LPD) such as a percutaneous leadless pacing system. Moreover, post-implant complications are reduced since LPDs do not require a lead in or near the left ventricle (LV); therefore, lead dislodgement is eliminated as a complication. Phrenic nerve stimulation is also unlikely because a LV lead is not employed for cardiac resynchronization therapy (CRT) delivery.

Exemplary methods, devices, and systems are described with reference to FIGS. 1-9. It is appreciated that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

This disclosure describes various techniques and systems in which the presence of ventricular dyssynchrony is determined to exist; and, in response, cardiac resynchronization therapy (CRT) is delivered to cardiac tissue via a leadless pacing device (LPD) that is controlled by a subcutaneous device (e.g. subcutaneous implantable cardioverter defibrillator (SICD), loop recorder etc. The presence of ventricular dyssynchrony is determined at implant or optionally post-implantation of the devices. For example, post-implant, ventricular dyssnchrony can be inferred to be present depending upon measured atrioventricular (AV) delays and/or P waves. The SICD can then send a control signal to the LPD to deliver therapeutic electrical stimulation (e.g. pacing pulses etc.) to the heart. The LPD can be implanted within a chamber of the heart or substernally/retrosternally.

FIG. 1 is a conceptual drawing illustrating an example system 10 that includes a subcutaneous device (SD) 30 (e.g. SICD, loop recorder (i.e. REVEAL®) etc.) implanted exterior to a rib cage of patient 14 and a leadless pacing device (LPD) 16 implanted within right ventricle 18 of patient 14. The SD 30 can be implanted external to a rib cage and within the vasculature. Additionally or alternatively, an implantable medical device can be implanted substernally/retrosternally, as described in U.S. Patent Application 61/819,946, entitled "IMPLANTABLE MEDICAL DEVICE SYSTEM HAVING IMPLANTABLE CARDIAC DEFIBRILLATOR SYSTEM AND SUBSTERNAL LEADLESS PACING DEVICE" filed May 6, 2013, incorporated by reference in its entirety. In the example of FIG. 1, system 10 includes LPD 16 and SD 30. External programmer 20 may be configured to communicate with one or both of LPD 16 and SD 30. Generally, there are no wires or other direct electrical (e.g., hardwired) connections between SD 30 and LPD 16. In this manner, any communication between SD 30 and LPD 16 may be described as "wireless" communication. Patient 14 is ordinarily, but not necessarily, a human patient.

Exemplary SD 30 includes a housing 32 configured to be subcutaneously implanted outside the rib cage of patient 14. The subcutaneous implantation location may be anterior to the cardiac notch, for example. In addition, housing 32 may carry three subcutaneous electrodes 34A-34C (collectively "electrodes 34"). In other examples, housing 32 may carry fewer or greater than three electrodes. Lead 36 may be configured to couple to housing 32 and extend from housing 32 to a different subcutaneous location within patient 14. For example, lead 36 may be tunneled laterally and posteriorly to the back of patient 14 at a location adjacent to a portion of a latissimus dorsi muscle. Lead 36 may carry electrode coil 38 along a length of lead 36 and sensing electrode 40 at a distal end of lead 36. SD 30 may be configured such that heart 12 may be disposed at least partially between housing 30 and electrode coil 38 of lead 36. In some examples, lead 36 may carry two or more electrode coils 38 and/or two or more sensing electrodes 40.

SD 30 may contain, within housing 32, signal processing and therapy delivery circuitry to detect cardiac conditions (e.g., ventricular dyssnchrony, arrhythmias such as bradycardia and tachycardia conditions etc.) and to communicate with LPD 16 to apply appropriate electrical stimuli (e.g. pacing and/or anti-tachyarrhythmia shock therapy (e.g., defibrillation or cardioversion shocking pulses)) to heart 12. SD 30 also may be configured to apply pacing pulses via one or more electrodes 34. SD 30 may be configured to apply the anti-tachyarrhythmia shock pulses between coil electrode 38 and one or more of electrodes 34 and/or the electrically conductive housing 32 (e.g., an additional can electrode) of SD 30. SD 30 may be configured to communicate with programmer 20 via an RF communication link, inductive coupling, or some other wireless communication protocol.

SD 30 differs from traditionally used ICDs in that housing 32 may be larger in size than the housing of a traditional ICD to accommodate larger capacity batteries, for example. In addition, SD 30 may be implanted subcutaneously whereas a traditional ICD may be implanted under muscle or deeper within patient 14. In other examples, housing 32 may be shaped or sized differently to be implanted subcutaneously instead of under a muscle or within deep tissue. Moreover, SD 30 does not include leads configured to be placed in the bloodstream (e.g., endocardial or epicardial leads). Instead, SD 30 may be configured to carry one or more electrodes (e.g., electrodes 34) on housing 32 together with one or more subcutaneous leads (e.g., lead 36) that carry defibrillation coil electrode 38 and sensing electrode 40. In other examples, lead 36 may include additional electrodes. These subcutaneously implanted electrodes of SD 30 may be used to provide therapies similar to that of traditional ICDs without invasive vascular leads. In other examples, the exact configuration, shape, and size of SD 30 may be varied for different applications or patients. Although SD 30 is generally described as including one or more electrodes, SD 30 may typically include at least two electrodes to deliver an electrical signal (e.g., therapy) and/or provide at least one sensing vector. Other exemplary SDs 30 can be used in combination with LPD 16. For example, SD 30 includes intravenously implanted device (IID), an ICD or a pacemaker or any other suitable device.

System 10 also includes one or more LPDs, such as LPD 16. LPD 16 may be, for example, an implantable leadless pacing device (e.g., a pacemaker, cardioverter, and/or defibrillator) that provides electrical signals to heart 12 via electrodes carried on the housing of LPD 16. In the example of FIG. 1, LPD 16 is implanted within left ventricle 16 of heart 12 to sense electrical activity of heart 12 and/or deliver electrical stimulation, e.g., CRT such as fusion pacing, to heart 12. Fusion pacing involves left ventricle (LV) 24 only pacing with an electrode on the LPD 16 in coordination with the intrinsic right ventricle (RV) activation. Alternatively, fusion pacing can involve pacing the RV with an electrode on the LPD 16 in coordination with the intrinsic LV activation. In this scenario, the LPD 16 is placed within the right ventricle 18.

LPD 16 is schematically shown in FIG. 1 attached to a wall of the left ventricle 24 via one or more fixation elements (e.g. tines, helix etc.) that penetrate the tissue. These fixation elements may secure LPD 16 to the cardiac tissue and retain an electrode (e.g., a cathode or an anode) in contact with the cardiac tissue. LPD 16 may also include one or more motion sensors (e.g., accelerometers) configured to detect and/or confirm cardiac conditions (e.g. ventricular dyssynchrony, tachyarrhythmias etc.) from these mechanical motions of heart 12. Since LPD 16 includes two or more electrodes carried on the exterior housing of LPD 16, no other leads or structures need to reside in other chambers of heart 12. However, in other examples, system 10 may include additional LPDs within respective chambers of heart 12 (e.g., left atrium 26, right atrium 22).

Using the electrodes carried on the housing of LPD 16, LPD 16 may be capable sensing intrinsic electrical signals, e.g., an electrocardiogram (ECG). SD 30 may similarly sense intrinsic electrical signals from the sensing vectors of electrodes 34, 38, and 40. These intrinsic signals may be electrical signals generated by cardiac muscle and indicative of depolarizations and repolarizations of heart 12 at various times during the cardiac cycle. LPD 16 may generate an electrogram from these cardiac signals that may be used by LPD 16 to detect cardiac conditions (e.g. ventricular dyssynchrony, arrhythmias, such as tachyarrhythmias), or identify other cardiac events, e.g., ventricle depolarizations or atrium depolarizations. LPD 16 may also measure impedances of the carried electrodes and/or determine capture thresholds of those electrodes intended to be in contact with cardiac tissue. In addition, LPD 16 may be configured to communicate with external programmer 20. The configurations of electrodes used by LPD 16 for sensing and pacing may be typically considered bipolar but unipolar may also be used.

External programmer 20 may be configured to communicate with one or both of SD 30 and LPD 16. In examples where external programmer 20 only communicates with one of SD 30 and LPD 16, the non-communicative device may receive instructions from or transmit data to the device in communication with programmer 20. In some examples, programmer 20 comprises a handheld computing device, computer workstation, or networked computing device. Programmer 20 may include a user interface that receives input from a user. In other examples, the user may also interact with programmer 20 remotely via a networked computing device. The user may interact with programmer 20 to communicate with LPD 16 and/or SD 30. For example, the user may interact with programmer 20 to send an interrogation request and retrieve therapy delivery data, update therapy parameters that define therapy, manage communication between LPD 16 and/or SD 30, or perform any other activities with respect to LPD 16 and/or SD 30. Although the user is a physician, technician, surgeon, electrophysiologist, or other healthcare professional, the user may be patient 14 in some examples.

Programmer 20 may also allow the user to define how LPD 16 and/or SD 30 senses electrical signals (e.g., ECGs), detects cardiac conditions (e.g. ventricular dyssynchrony, arrhythmias etc.), delivers therapy, and communicates with other devices of system 10. For example, programmer 20 may be used to change detection parameters. In another example, programmer 20 may be used to manage therapy parameters that define therapies such as CRT. Moreover, programmer 20 may be used to alter communication protocols between LPD 16 and SD 30. For example, programmer 20 may instruct LPD 16 and/or SD 30 to switch between one-way and two-way communication and/or change which of LPD 16 and/or SD 30 are tasked with initial detection of a cardiac condition.

Programmer 20 may communicate with LPD 16 and/or SD 30 via wireless communication using any techniques known in the art. Examples of communication techniques may include, for example, radiofrequency (RF) telemetry, but other techniques are also contemplated. In some examples, programmer 20 may include a programming head that may be placed proximate to the patient's body near the LPD 16 and/or SD 30 implant site in order to improve the quality or security of communication between LPD 16 and/or SD 30 and programmer 20.

LPD 16 and SD 30 may engage in communication to facilitate the appropriate detection of ventricular dyssynchrony and/or delivery of CRT. The communication may include one-way communication in which one device is configured to transmit communication messages and the other device is configured to receive those messages. The communication may instead include two-way communication in which each device is configured to transmit and receive communication messages. LPD 16 and SD 30 may be configured to communicate with each other provide alternative electrical stimulation therapies.

Although LPD 16 may at least partially determine whether or not LPD 16 delivers CRT or another therapy to patient 14, LPD 16 may perform one or more functions in response to receiving a request from SD 30 and without any further analysis by LPD 16. In this manner, SD 30 may act as a master device and LPD 16 may act as a slave device. In this configuration, LPD 16 passively senses. Specifically, a WT mode is employed as a trigger mode to pace in synchrony. In one or more embodiments, the LPD 16 can be configured to actively sense.

Figure 2A:
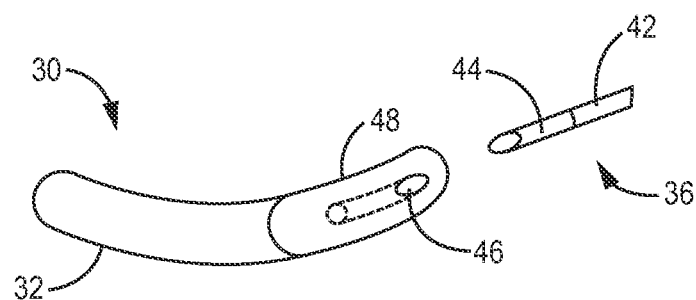
FIGS. 2A and 2B are conceptual drawings illustrating different views of the example SICD of FIG. 1
Figure 2B:
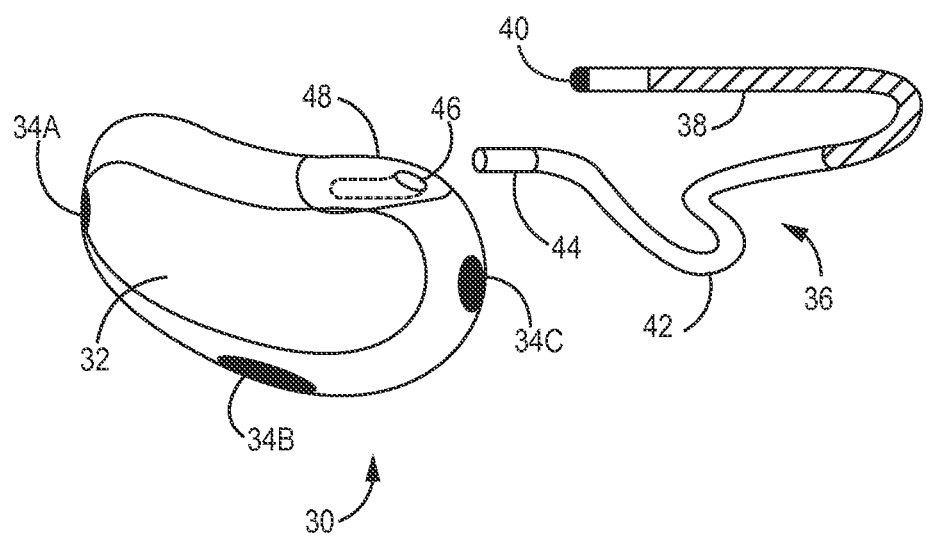

FIGS. 2A and 2B are conceptual drawings illustrating different views of SD 30 of FIG. 1. FIG. 2A is a top view of SD 30, and FIG. 2B is a front view of SD 30. In the example of FIGS. 2A and 2B, housing 32 may be constructed as an ovoid with a substantially kidney-shaped profile. The ovoid shape of housing 32 may promote ease of subcutaneous implantation and may minimize patient discomfort during normal body movement and flexing of the thoracic musculature. In other examples, housing 32 may be constructed with different shapes intended for different implant locations and/or to house different components, subcutaneous leads, or configurations for electrodes 34 FIG. 2B.

Housing 32 may contain the electronic circuitry of SD 30. Header 48 and connector 46 may provide an electrical connection between distal electrode coil 38 and distal sensing electrode 40 of lead 36 and the circuitry within housing 32. Subcutaneous lead 36 may include distal defibrillation coil electrode 38, distal sensing electrode 40, insulated flexible lead body 42 and proximal connector pin 44. Distal sensing electrode 40 may be sized appropriately to match the sensing impedance of electrodes 34A-34C to be used in combination.

In some examples, electrodes 34 are each welded into place on a flattened periphery of housing 32 and are connected to electronic circuitry inside housing 32. Electrodes 34 may be constructed of flat plates, or alternatively, spiral electrodes (as described in U.S. Pat. No. 6,512,940, incorporated herein in its entirety) and mounted in a non-conductive surround shroud (as described in U.S. Pat. Nos. 6,522,915 and 6,622,046, both incorporated herein in their entirety). Electrodes 34 shown in FIG. 2B may be positioned on housing 32 to form orthogonal signal vectors. However, electrodes 34 may be positioned to form any non-orthogonal signal vectors in other examples. In addition, housing 32 may include fewer or greater than three electrodes. Moreover, housing 32 may be configured as an electrically conductive surface and operate as an electrode. Housing 32 may be referred to as a "can electrode" or used as an indifferent electrode. In some examples, housing 32 may be used as an electrode with coil electrode 38 during delivery of (electrical stimuli e.g. pacing pulses, anti-tachyarrhythmia shock).

Figure 3:
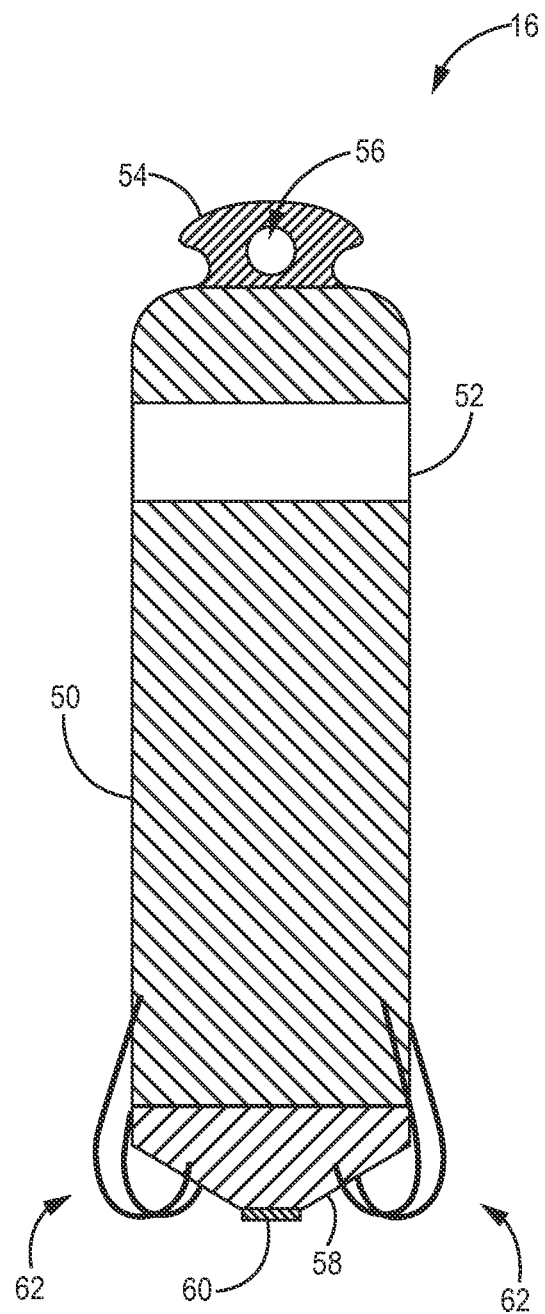
FIG. 3 is a conceptual drawing illustrating the example LPD of FIG. 1.

FIG. 3 is a conceptual drawing illustrating example LPD 16 of FIG. 1. As shown in FIG. 3, LPD 16 includes case 50, cap 58, electrode 60, electrode 52, fixation mechanisms 62, flange 54, and opening 56. Together, case 50 and cap 58 may be considered the housing of LPD 16. In this manner, case 50 and cap 58 may enclose and protect the various electrical components within LPD 16. Case 50 may enclose substantially all of the electrical components, and cap 58 may seal case 50 and create the hermetically sealed housing of LPD 16. Although LPD 16 is generally described as including one or more electrodes, LPD 16 may typically include at least two electrodes (e.g., electrodes 52 and 60) to deliver an electrical signal (e.g., therapy such as CRT) and/or provide at least one sensing vector. Electrodes 52 and 60 are carried on the housing created by case 50 and cap 58. In this manner, electrodes 52 and 60 may be considered leadless electrodes. In the example of FIG. 3, electrode 60 is disposed on the exterior surface of cap 58. Electrode 60 may be a circular electrode positioned to contact cardiac tissue upon implantation. Electrode 52 may be a ring or cylindrical electrode disposed on the exterior surface of case 50. Both case 50 and cap 58 may be electrically insulating. Electrode 60 may be used as a cathode and electrode 52 may be used as an anode, or vice versa, for delivering CRT or other appropriate cardiac therapy (ATP, shock etc.). However, electrodes 52 and 60 may be used in any stimulation configuration. In addition, electrodes 52 and 60 may be used to detect intrinsic electrical signals from cardiac muscle. In other examples, LPD 16 may include three or more electrodes, where each electrode may deliver therapy and/or detect intrinsic signals. CRT delivered by LPD 16 may be considered to be "painless" to patient 14 or even undetectable by patient 14 since the electrical stimulation occurs very close to or at cardiac muscle and at relatively low energy levels compared with alternative devices.

Fixation mechanisms 62 may attach LPD 16 to cardiac tissue. Fixation mechanisms 62 may be active fixation tines, screws, clamps, adhesive members, or any other types of attaching a device to tissue. As shown in the example of FIG. 3, fixation mechanisms 62 may be constructed of a memory material that retains a preformed shape. During implantation, fixation mechanisms 62 may be flexed forward to pierce tissue and allowed to flex back towards case 50. In this manner, fixation mechanisms 62 may be embedded within the target tissue.

Flange 54 may be provided on one end of case 50 to enable tethering or extraction of LPD 16. For example, a suture or other device may be inserted around flange 54 and/or through opening 56 and attached to tissue. In this manner, flange 54 may provide a secondary attachment structure to tether or retain LPD 16 within heart 12 if fixation mechanisms 62 fail. Flange 54 and/or opening 56 may also be used to extract LPD 16 once the LPD needs to be explanted (or removed) from patient 14 if such action is deemed necessary.

In another example, LPD 16 may be configured to be implanted external to heart 12, e.g., near or attached to the epicardium of heart 12. An electrode carried by the housing of the fusion pacing LPD 16 may be placed in contact with the epicardium and/or one or more electrodes placed in contact with the epicardium at locations sufficient to provide therapy (e.g., on external surfaces of the left and/or right ventricles). In any example, SD 30 may communicate with one or more leadless or leaded devices implanted internal or external to heart 12.

Figure 4:
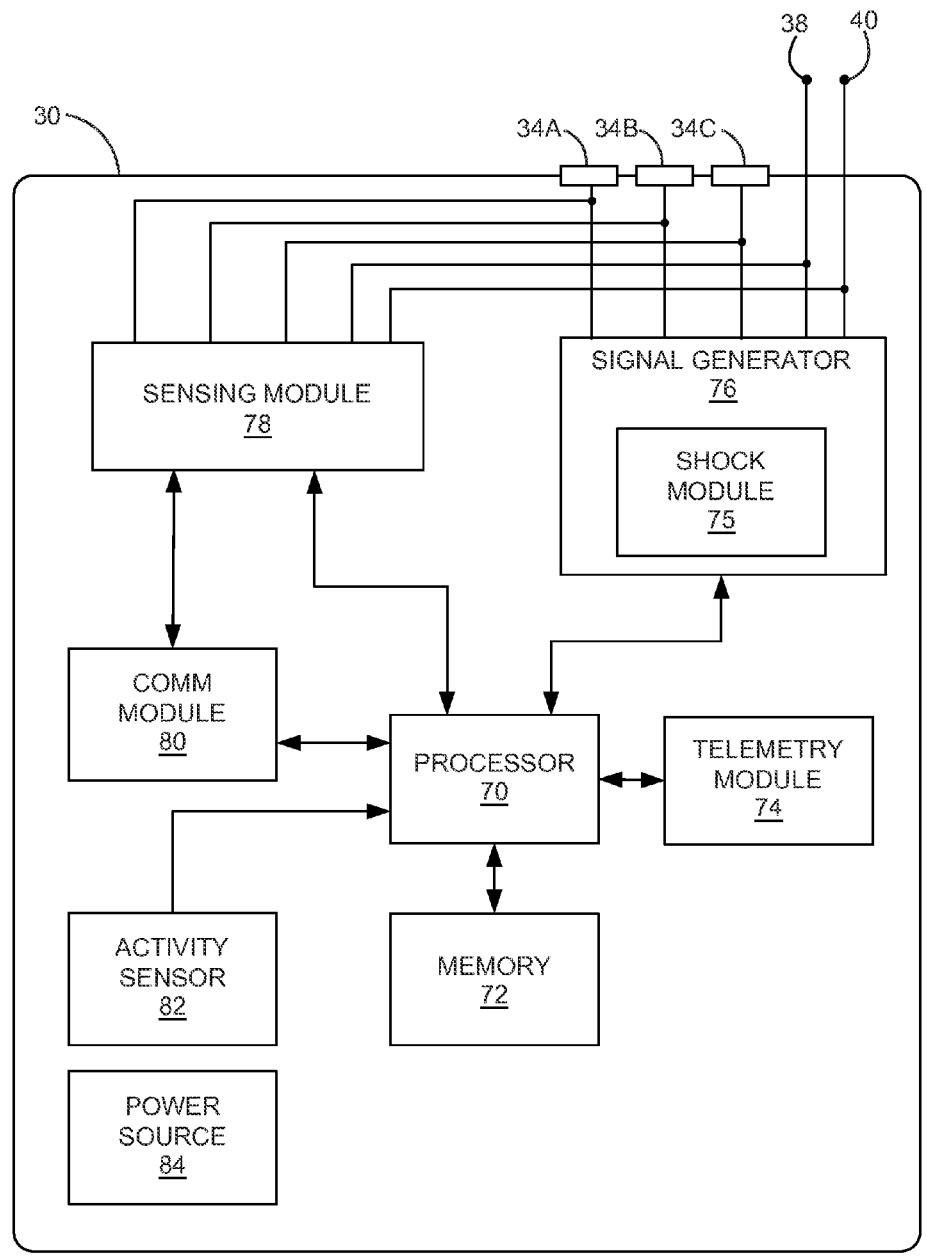
FIG. 4 is a functional block diagram illustrating an example configuration of the SICD of FIG. 1.

FIG. 4 is a functional block diagram illustrating an example configuration of SD 30 of FIG. 1. In the illustrated example, SD 30 includes a processor 70, memory 72, shock module 75, signal generator 76, sensing module 78, telemetry module 74, communication module 80, activity sensor 82, and power source 84. Memory 72 includes computer-readable instructions that, when executed by processor 70, cause SD 30 and processor 70 to perform various functions attributed to SD 30 and processor 70 herein (e.g., detection of ventricular dyssynchrony, communication with LPD 16, and/or delivery of anti-tachyarrhythmia shock therapy, if needed). Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 70 may include any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof.

Processor 70 controls signal generator 76 to deliver stimulation therapy to heart 12 according to a therapy parameters, which may be stored in memory 72. For example, processor 70 may control signal generator 76 to deliver electrical pulses (e.g., shock pulses) with the amplitudes, pulse widths, frequency, or electrode polarities specified by the therapy parameters. In this manner, signal generator 76 may deliver electrical pulses to heart 12 via electrodes 34, 38, and/or 40. In addition, housing 30 may be configured as an electrode and coupled to signal generator 76 and/or sensing module 78. SD 30 may use any combination of electrodes to deliver anti-tachycardia therapy and/or detect electrical signals from patient 14. However, in general, coil electrode 38 may be used to deliver an anti-tachyarrhythmia shock, if necessary.

Signal generator 76 may also include shock module 75. Shock module 75 may include circuitry and/or capacitors required to deliver an anti-tachyarrhythmia shock. For example, signal generator 76 may charge shock module 75 to prepare for delivering a shock. Shock module 75 may then discharge to enable signal generator 76 to deliver the shock to patient 14 via one or more electrodes. In other examples, shock module 75 may be located within SD 30 but outside of signal generator 76.

Signal generator 76 is electrically coupled to electrodes 34, 38, and 40. In the illustrated example, signal generator 76 is configured to generate and deliver electrical stimuli (e.g. anti-tachyarrhythmia shock therapy) to heart 12. For example, signal generator 76 may, using shock module 75, deliver shocks to heart 12 via a subset of electrodes 34, 38, and 40. In some examples, signal generator 76 may deliver pacing stimulation, and cardioversion or defibrillation shocks in the form of electrical pulses. In other examples, signal generator may deliver one or more of these types of stimulation or shocks in the form of other signals, such as sine waves, square waves, or other substantially continuous time signals.

Signal generator 76 may include a switch module and processor 70 may use the switch module to select, e.g., via a data/address bus, which of the available electrodes are used to deliver shock and/or pacing pulses. The switch module may include a switch array, switch matrix, multiplexer, or any other type of switching device suitable to selectively couple stimulation energy to selected electrodes.

Electrical sensing module 78 may be configured to monitor signals from at least one of electrodes 34, 38, and 40 in order to monitor electrical activity of heart 12, impedance, or other electrical phenomenon. Sensing may be done to determine heart rates or heart rate variability, or to detect arrhythmias (e.g., tachyarrhythmia) or other electrical signals. Sensing module 78 may also include a switch module to select which of the available electrodes are used to sense the heart activity, depending upon which electrode combination, or electrode vector, is used in the current sensing configuration. In examples with several electrodes, processor 70 may select the electrodes that function as sense electrodes, i.e., select the sensing configuration, via the switch module within sensing module 78. Sensing module 78 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 70, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processor 70 may control the functionality of sensing module 78 by providing signals via a data/address bus.

Processor 70 may include a timing and control module, which may be embodied as hardware, firmware, software, or any combination thereof. The timing and control module may comprise a dedicated hardware circuit, such as an ASIC, separate from other processor 70 components, such as a microprocessor, or a software module executed by a component of processor 70, which may be a microprocessor or ASIC. The timing and control module may implement programmable counters. If SD 30 is configured to generate and deliver pacing pulses to heart 12, such counters may control the basic time intervals associated with DDD, VVI, DVI, VDD, AAI, DDI, DDDR, VVIR, DVIR, VDDR, AAIR, DDIR and other modes of pacing.

Intervals defined by the timing and control module within processor 70 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing module 78 for a time interval during and after delivery of electrical stimulation to heart 12. The durations of these intervals may be determined by processor 70 in response to stored data in memory 72. The timing and control module of processor 70 may also determine the amplitude of the cardiac pacing pulses.

Interval counters implemented by the timing and control module of processor 70 may be reset upon sensing of R-waves and P-waves with detection channels of sensing module 78. The value of the count present in the interval counters when reset by sensed R-waves and P-waves may be used by processor 70 to measure the durations of R-R intervals, P-P intervals, P-R intervals and R-P intervals, which are measurements that may be stored in memory 72. In some examples, processor 70 may determine that ventricular dyssynchrony has occurred based on AV interval and P-wave width measurements. Ventricular dyssynchrony is automatically addressed by updating AV delays every minute based on AV interval and Pwave width measurements.

In some examples, communication module 80 may be used to detect communication signals from LPD 16. LPD 16 may not include telemetry circuitry. Instead, LPD 16 may generate electrical signals via one or more electrodes with amplitudes and/or patterns representative of information to be sent to SD 30. The electrical signals may be carried by pacing pulses or separate communication signals configured to be detected by SD 30. In this manner, communication module 80 may be configured to monitor signals sensed by sensing module 78 and determine when a communication message is received from LPD 16.

In other examples, SD 30 may also transmit communication messages to LPD 16 using electrical signals from one or more of electrodes 34, 38, and 40. In this case, communication module 80 may be coupled to signal generator 76 to control the parameters of generated electrical signals or pulses. Alternatively, processor 70 may detect communications via sensing module 78 and/or generate communications for deliver via signal generator 76. Although communication module 80 may be used to communicate using electrical signals via electrodes 34, 38 and 40, communication module 80 may alternatively or in addition use wireless protocols such as RF telemetry to communicate with LPD 16 or other medical devices. In some examples, telemetry module 74 may include this wireless communication functionality.

Memory 72 may be configured to store a variety of operational parameters, therapy parameters, sensed and detected data, and any other information related to the monitoring, therapy and treatment of patient 14. Memory 72 may store, for example, thresholds and parameters indicative of cardiac conditions such as ventricular dyssynchrony and/or therapy parameter values that at least partially define delivered CRT such as fusion pacing. In some examples, memory 72 may also store communications transmitted to and/or received from LPD 16.

Activity sensor 82 may be contained within the housing of SD 30 and include one or more accelerometers or other devices capable of detecting motion and/or position of SD 30. For example, activity sensor 82 may include a 3-axis accelerometer that is configured to detect accelerations in any direction in space. Accelerations detected by activity sensor 82 may be used by processor 70 to identify potential noise in signals detected by sensing module 78 and/or confirm the detection of arrhythmias or other patient conditions.

Telemetry module 74 includes any suitable hardware, firmware, software or any combination thereof for communicating with another device, such as programmer 20 (FIG. 1). As described herein, telemetry module 74 may transmit generated or received arrhythmia data, therapy parameter values, communications between SD 30 and LPD 16, or any other information. For example, telemetry module 74 may transmit information representative of sensed physiological data such as R-R intervals or any other data that may be used by LPD 16 to determine a condition of patient 14. Telemetry module 74 may also be used to receive updated therapy parameters from programmer 20. Under the control of processor 70, telemetry module 74 may receive downlink telemetry from and send uplink telemetry to programmer 20 with the aid of an antenna, which may be internal and/or external. Processor 70 may provide the data to be uplinked to programmer 20 and the control signals for the telemetry circuit within telemetry module 74, e.g., via an address/data bus. In some examples, telemetry module 74 may provide received data to processor 70 via a multiplexer. In some examples, SD 30 may signal programmer 20 to further communicate with and pass the alert through a network such as the Medtronic CareLink® Network developed by Medtronic, Inc., of Minneapolis, Minn., or some other network linking patient 14 to a clinician. SD 30 may spontaneously transmit the diagnostic information to the network or in response to an interrogation request from a user.

Power source 84 may be any type of device that is configured to hold a charge to operate the circuitry of SICD. Power source 84 may be provided as a rechargeable or non-rechargeable battery. In other examples, power source 84 may also incorporate an energy scavenging system that stores electrical energy from movement of SD 30 within patient 14.

There may be numerous variations to the configuration of SD 30, as described herein. In the examples of FIGS. 2A, 2B, and 4, SD 30 may include housing 32 configured to be implanted in patient 14 external to a rib cage of patient 14, one or more electrodes (e.g., electrodes 34, 38, and 40) configured to be disposed external to the rib cage, and shock module 75 configured to at least partially deliver anti-tachyarrhythmia shock therapy to patient 14 via the one or more electrodes.

SD 30 may also include communication module 80 configured to transmit and/or receive communication messages between LPD 16 configured to be implanted within heart 12 of patient 14 and a sensing module 78 configured to sense an electrical signal from heart 12 of patient 14 via the one or more electrodes. Further, SD 30 may include one or more processors 70 configured to detect a ventricular dyssynchrony within the sensed electrical signal and determine, based on the detected ventricular dyssynchrony, to deliver CRT to patient 14 to treat the detected ventricular dyssynchrony. Processor 70 may also be configured to transmit, via communication module 80 and prior to delivering CRT, a communication message to LPD 16 requesting LPD 16 deliver fusion pacing to heart 12 of patient 14.

Figure 5:
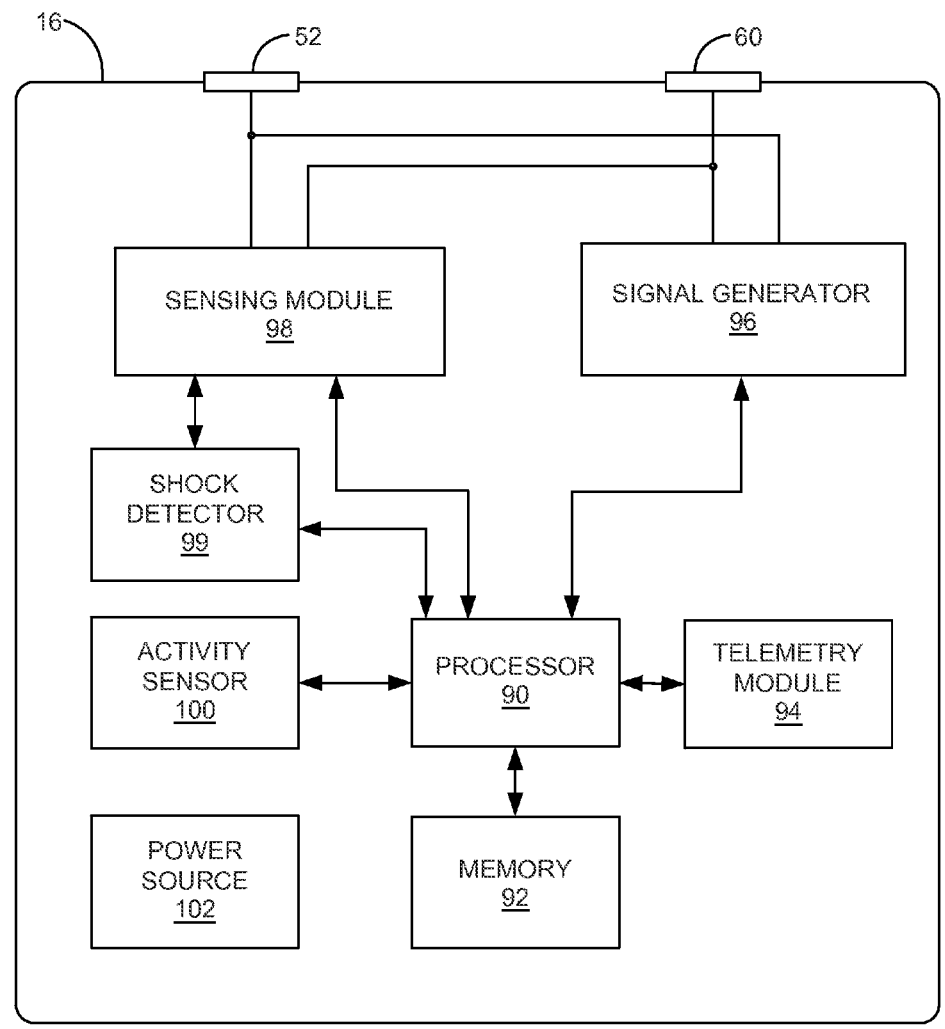
FIG. 5 is a functional block diagram illustrating an example configuration of the LPD of FIG. 1.

FIG. 5 is a functional block diagram illustrating an example configuration of LPD 16 of FIG. 1. In the illustrated example, LPD 16 includes a processor 90, memory 92, signal generator 96, sensing module 98, shock detector 99, activity sensor 100, telemetry module 94, and power source 102. Memory 92 includes computer-readable instructions that, when executed by processor 90, cause LPD 16 and processor 90 to perform various functions attributed to LPD 16 and processor 90 herein (e.g., detecting ventricular dyssnchrony, arrhythmias, communicating with SD 30, and delivering anti-tachycardia pacing and post-shock pacing). Memory 92 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 90 may include any one or more of a microprocessor, a controller, a digital signal processor (DSP), an application specific integrated circuit (ASIC), a field-programmable gate array (FPGA), or equivalent discrete or analog logic circuitry. In some examples, processor 90 may include multiple components, such as any combination of one or more microprocessors, one or more controllers, one or more DSPs, one or more ASICs, or one or more FPGAs, as well as other discrete or integrated logic circuitry. The functions attributed to processor 90 herein may be embodied as software, firmware, hardware or any combination thereof.

Processor 90 controls signal generator 96 to deliver stimulation therapy to heart 12 according to a therapy parameters, which may be stored in memory 92. For example, processor 90 may control signal generator 96 to deliver electrical pulses with the amplitudes, pulse widths, frequency, or electrode polarities specified by the therapy parameters. In this manner, signal generator 96 may deliver pacing pulses (e.g., fusion pacing) to heart 12 via electrodes 52 and 60. Although LPD 16 may only include two electrodes, e.g., electrodes 52 and 60, LPD 16 may utilize three or more electrodes in other examples. LPD 16 may use any combination of electrodes to deliver therapy and/or detect electrical signals from patient 14.

Signal generator 96 is electrically coupled to electrodes 52 and 60 carried on the housing of LPD 16. In the illustrated example, signal generator 96 is configured to generate and deliver electrical stimulation therapy to heart 12. For example, signal generator 96 may deliver pulses to a portion of cardiac muscle within heart 12 via electrodes 52 and 60. In some examples, signal generator 96 may deliver pacing stimulation in the form of electrical pulses. In other examples, signal generator may deliver one or more of these types of stimulation in the form of other signals, such as sine waves, square waves, or other substantially continuous time signals. Although LPD 16 is generally described has delivering pacing pulses, LPD 16 may deliver cardioversion or defibrillation pulses in other examples.

Fusion pacing may be delivered to patient 14 as defined by a set of parameters. These parameters may include pulse intervals, pulse width, current and/or voltage amplitudes, and durations for each pacing mode.

Signal generator 96 may also include circuitry for measuring the capture threshold of one or both electrodes 52 and 60. The capture threshold may indicate the voltage necessary to induce depolarization of the surrounding cardiac muscle. For example, signal generator 96 may measure the voltage of pacing signals needed to induce synchronized ventricular contractions. In examples in which LPD 16 includes more than two electrodes, signal generator 96 may include a switch module and processor 90 may use the switch module to select, e.g., via a data/address bus, which of the available electrodes are used to deliver pacing pulses. The switch module may include a switch array, switch matrix, multiplexer, or any other type of switching device suitable to selectively couple stimulation energy to selected electrodes. In the instance that the capture threshold exceeds useable limits, processor 90 may withhold delivery of therapeutic pacing. In addition, processor 90 may transmit communication to SD 30 if pacing cannot be delivered.

Electrical sensing module 98 monitors signals from at least one of electrodes 52 and 60 in order to monitor electrical activity of heart 12, impedance, or other electrical phenomenon. Sensing may be done to determine heart rates or heart rate variability, or to detect ventricular dyssynchrony, arrhythmias (e.g., tachyarrhythmias) or other electrical signals. Sensing module 98 may also include a switch module to select which of the available electrodes (or electrode polarity) are used to sense the heart activity, depending upon which electrode combination, or electrode vector, is used in the current sensing configuration. In examples with several electrodes, processor 90 may select the electrodes that function as sense electrodes, i.e., select the sensing configuration, via the switch module within sensing module 98. Sensing module 98 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 90, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processor 90 may control the functionality of sensing module 98 by providing signals via a data/address bus.

Processor 90 may include a timing and control module, which may be embodied as hardware, firmware, software, or any combination thereof. The timing and control module may comprise a dedicated hardware circuit, such as an ASIC, separate from other processor 90 components, such as a microprocessor, or a software module executed by a component of processor 90, which may be a microprocessor or ASIC. The timing and control module may implement programmable counters. If LPD 16 is configured to generate and deliver pacing pulses to heart 12, such counters may control the basic time intervals associated with DDD, VVI, DVI, VDD, AAI, DDI, DDDR, VVIR, DVIR, VDDR, AAIR, DDIR and other modes of pacing. Example LPDs that may deliver pacing using such modes are described in U.S. patent application Ser. No. 13/665,492 to Bonner et al., entitled, "LEADLESS PACEMAKER SYSTEM," and filed on Oct. 31, 2012, or in U.S. patent application Ser. No. 13/665,601 to Bonner et al., entitled, "LEADLESS PACEMAKER SYSTEM," and filed on Oct. 31, 2012. U.S. patent application Ser. No. 13/665,492 to Bonner et al. and U.S. patent Ser. No. 13/665,601 to Bonner et al. are both incorporated herein by reference in their entireties.

In addition to detecting and identifying specific types of cardiac rhythms (types of cardiac events), sensing module 98 may also sample the detected intrinsic signals to generate an electrogram or other time-based indication of cardiac events. Processor 90 may also be able to coordinate the delivery of pacing pulses from different LPDs implanted in different chambers of heart 12, such as an LPD implanted in the other ventricle. For example, processor 90 may identify delivered pulses from other LPDs via sensing module 98 and updating pulse timing. In other examples, LPDs may communicate with each other via telemetry module 94 and/or instructions over a carrier wave (such as a stimulation waveform).

Memory 92 may be configured to store a variety of operational parameters, therapy parameters, sensed and detected data, and any other information related to the therapy and treatment of patient 14. In the example of FIG. 5, memory 92 may store sensed ECGs, detected arrhythmias, communications from SD 30, and therapy parameters. In other examples, memory 92 may act as a temporary buffer for storing data until it can be uploaded to SD 30, another implanted device, or programmer 20.

Activity sensor 100 may be contained within the housing of LPD 16 and include one or more accelerometers or other devices capable of detecting motion and/or position of LPD 16. For example, activity sensor 100 may include a 3-axis accelerometer that is configured to detect accelerations in any direction in space. Specifically, the 3-axis accelerator may be used to detect LPD 16 motion that may be indicative of cardiac events and/or noise. For example, processor 16 may monitor the accelerations from activity sensor 100 to confirm or detect arrhythmias. Since LPD 16 may move with a chamber wall of heart 12, the detected changes in acceleration may also be indicative of contractions. Therefore, LPD 16 may be configured to identify heart rates and confirm ventricular dyssynchrony sensed via sensing module 98.

Telemetry module 94 includes any suitable hardware, firmware, software or any combination thereof for communicating with another device, such as programmer 20 or SD 30 (FIG. 1). Under the control of processor 90, telemetry module 94 may receive downlink telemetry from and send uplink telemetry to programmer 20 with the aid of an antenna, which may be internal and/or external. Processor 90 may provide the data to be uplinked to programmer 20 and the control signals for the telemetry circuit within telemetry module 94, e.g., via an address/data bus. In some examples, telemetry module 94 may provide received data to processor 90 via a multiplexer.

In some examples, LPD 16 may signal programmer 20 to further communicate with and pass the alert through a network such as the Medtronic CareLink® Network developed by Medtronic, Inc., of Minneapolis, Minn., or some other network linking patient 14 to a clinician. LPD 16 may spontaneously transmit information to the network or in response to an interrogation request from a user.

In other examples, processor 90 may be configured to transmit information to another device, such as SD 30 using electrodes 52 and 60. For example, processor 90 may control signal generator 96 to generate electrical signals representative of commands such as the detection of ventricular dyssynchrony, confirmation that ventricular dyssynchrony has been detected, a request to monitor electrical signals for ventricular dyssynchrony, or even signals to "wake up" an SICD in a sleep mode. In other examples, processor 90 may cause telemetry module 94 to transmit information representative of sensed physiological data such as R-R intervals or any other data that may be used by SD 30 to determine a condition of patient 14 (e.g., whether or not patient 14 is experiencing ventricular dyssynchrony). The communication may be in the form of dedicated communication signals.

Alternatively, processor 90 may communicate with SD 30 by delivering pacing pulses at specific intervals that would be identifiable by SD 30 as non-physiologic and intended to convey information. In other words, these pulses intended for communication with SD 30. SD 30 may be configured to identify, or distinguish, these pulses from signals indicative of normal or non-normal heart beats, signals indicative of ectopic or non-ectopic heart beats, signals indicative of noise (e.g., skeletal muscle noise), or any other signals indicative of typically physiological or therapeutic electrical signals. The communication pulses may or may not be therapeutic pulses or signals. SD 30 may detect the intervals between these pulses as code for specific messages from LPD 16. For example, the pacing pulses may be varied and/or repeated in certain patterns detectable by SD 30 and still therapeutic. LPD 16 may also be configured to detect such communication messages via electrodes 52 and 60. Processor 90 may monitor sensing module 98 for such communications. Alternatively, LPD 16 may include a communication module, similar to communication module 80 of FIG. 4, to detect any communications received via sensing module 98. In any example, LPD 16 may be configured for one-way communication to or from another device such as SD 30 or two-way communication with another device such as SD 30 using any type of communication protocol.

Power source 102 may be any type of device that is configured to hold a charge to operate the circuitry of LPD 16. Power source 102 may be provided as a rechargeable or non-rechargeable battery. In other example, power source 102 may incorporate an energy scavenging system that stores electrical energy from movement of LPD 16 within patient 14.

There may be numerous variations to the configuration of LPD 16, as described herein. In one example, LPD 16 includes a housing configured to be implanted within heart 12 of patient 14, one or more electrodes (e.g., electrodes 52 and 60) coupled to the housing, fixation mechanism 62 configured to attach the housing to tissue of heart 12, sensing module 98 configured to sense an electrical signal from heart 12 of patient 14 via the one or more electrodes, and signal generator 96 configured to deliver therapy to heart 12 of patient 14 via the one or more electrodes. LPD 16 may also include processor 90 configured to receive a communication message from SD 30 requesting LPD 16 deliver CRT to heart 12, where SD 30 is configured to be implanted exterior to a rib cage of patient 14. Processor 90 may also be configured to determine, based on the sensed electrical signal, whether to deliver CRT to heart 12, and, in response to the determination, command signal generator 96 to deliver the CRT therapy. Processor 90 may also be configured to control signal generator 96 to deliver post-shock pacing to patient 14 in response to shock detector 99 detecting an anti-tachyarrhythmia shock.

Figure 6:
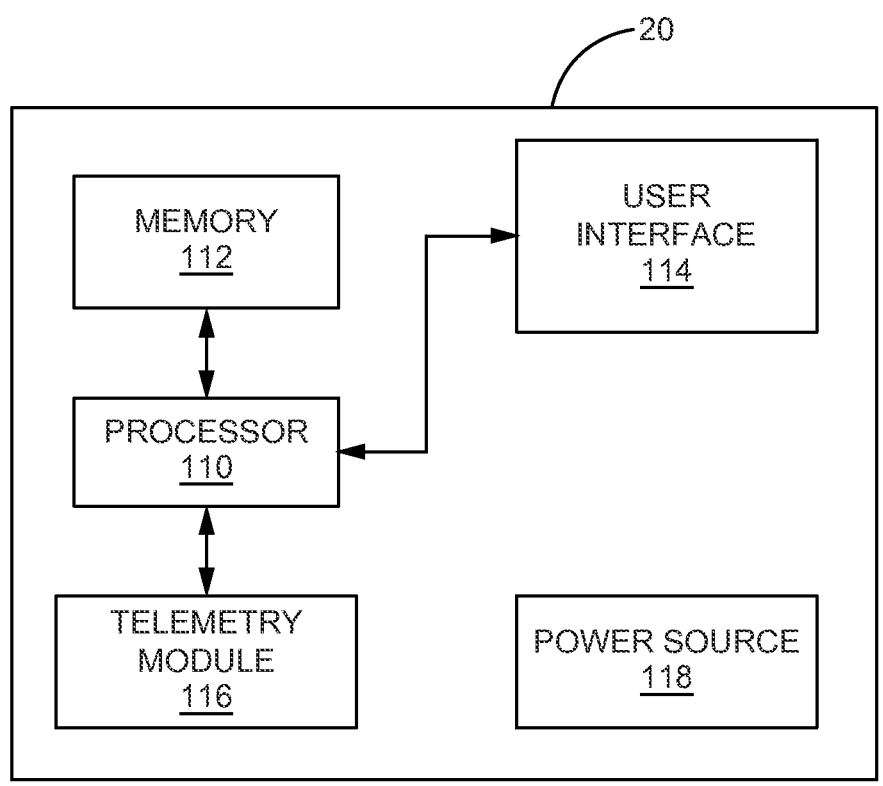
FIG. 6 is a functional block diagram illustrating an example configuration of the programmer of FIG. 1.

FIG. 6 is a functional block diagram illustrating an example configuration of external programmer 20 of FIG. 1. As shown in FIG. 6, programmer 20 may include a processor 110, memory 112, user interface 114, telemetry module 116, and power source 118. Programmer 20 may be a dedicated hardware device with dedicated software for programming of LPD 16 and/or SD 30. Alternatively, programmer 20 may be an off-the-shelf computing device running an application that enables programmer 20 to program LPD 16 and/or SD 30.

A user may use programmer 20 to configure the operational parameters of and retrieve data from LPD 16 and/or SD 30 (FIG. 1). In one example, programmer 20 may communicate directly to both LPD 16 and SD 30. In other examples, programmer may communicate to one of LPD 16 or SD 30, and that device may relay any instructions or information to or from the other device. The clinician may interact with programmer 20 via user interface 114, which may include display to present graphical user interface to a user, and a keypad or another mechanism for receiving input from a user. In addition, the user may receive an alert or notification from SD 30 indicating that a shock has been delivered, any other therapy has been delivered, or any problems or issues related to the treatment of patient 14.

Processor 110 can take the form one or more microprocessors, DSPs, ASICs, FPGAs, programmable logic circuitry, or the like, and the functions attributed to processor 110 herein may be embodied as hardware, firmware, software or any combination thereof. Memory 112 may store instructions that cause processor 110 to provide the functionality ascribed to programmer 20 herein, and information used by processor 110 to provide the functionality ascribed to programmer 20 herein. Memory 112 may include any fixed or removable magnetic, optical, or electrical media, such as RAM, ROM, CD-ROM, hard or floppy magnetic disks, EEPROM, or the like. Memory 112 may also include a removable memory portion that may be used to provide memory updates or increases in memory capacities. A removable memory may also allow patient data to be easily transferred to another computing device, or to be removed before programmer 20 is used to program therapy for another patient.

Programmer 20 may communicate wirelessly with LPD 16 and/or SD 30, such as using RF communication or proximal inductive interaction. This wireless communication is possible through the use of telemetry module 116, which may be coupled to an internal antenna or an external antenna. An external antenna that is coupled to programmer 20 may correspond to the programming head that may be placed over heart 12 or the location of the intend implant, as described above with reference to FIG. 1. Telemetry module 116 may be similar to telemetry modules 74 and 94 of respective FIGS. 4 and 5.

Telemetry module 116 may also be configured to communicate with another computing device via wireless communication techniques, or direct communication through a wired connection. Examples of local wireless communication techniques that may be employed to facilitate communication between programmer 20 and another computing device include RF communication according to the 802.11 or Bluetooth specification sets, infrared communication, e.g., according to the IrDA standard, or other standard or proprietary telemetry protocols. An additional computing device in communication with programmer 20 may be a networked device such as a server capable of processing information retrieved from LPD 16. In other examples, LPD 16 may not use a shock detector to time the beginning or ending of post-shock pacing. Instead, LPD 16 may determine when to deliver post-shock pacing based on a command from SD 30. For example, SD 30 may determine that a shock will be delivered and transmit a shock imminent command to LPD 16. In response to receiving the shock imminent command, LPD 16 may enter a shock state for a predetermined period of time. This predetermined period of time may be stored in memory 92 or sent along with the shock imminent command from SD 30. The predetermined period of time may have a sufficient duration such that any shock would be delivered prior to the predetermined period expiring. In response to the predetermined period elapsing, LPD 16 may exit the shock state and enter a post-shock pacing state in which LPD 16 delivers post-shock pacing and/or first determines whether post-shock pacing is needed.

Figure 7:
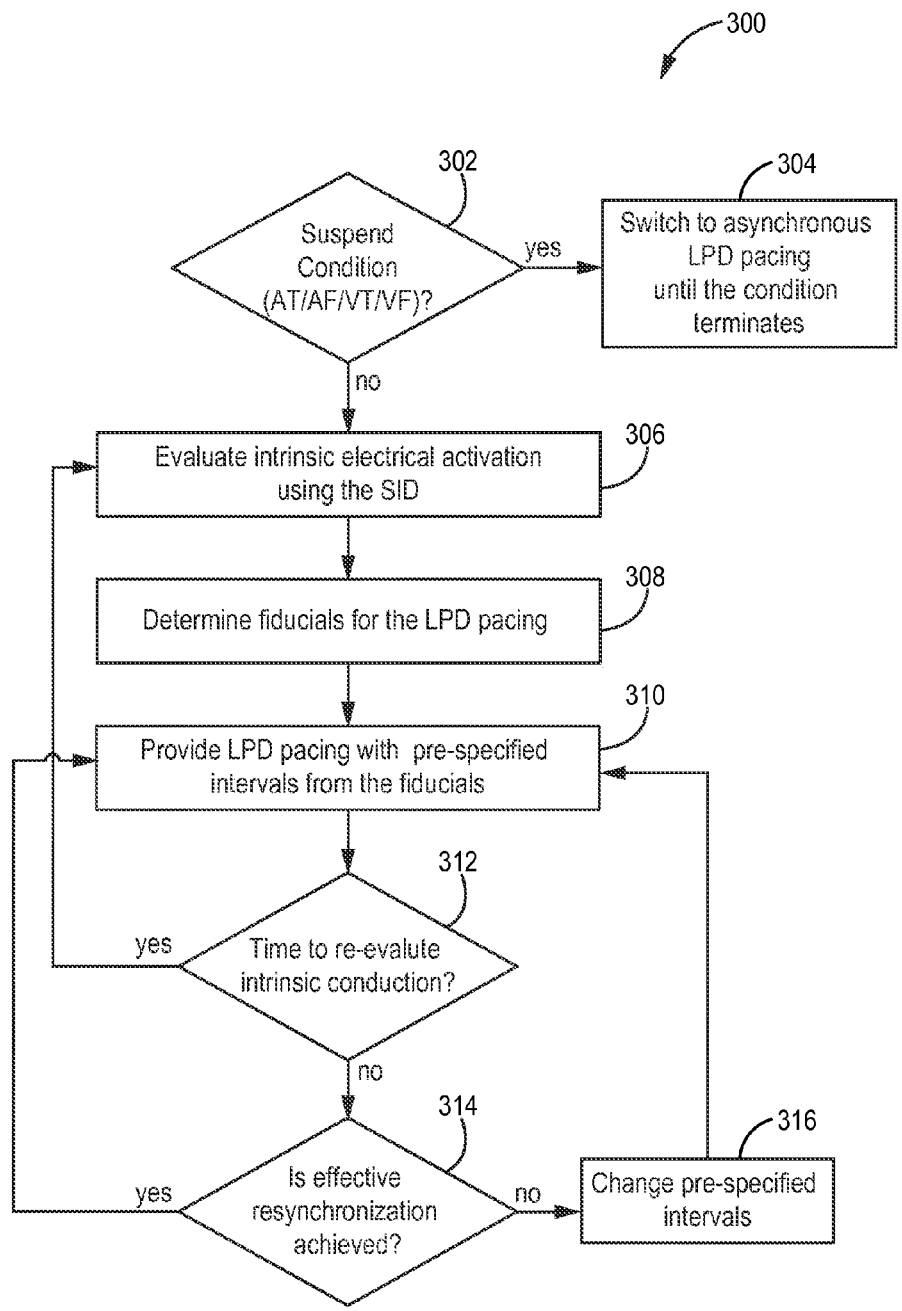
FIG. 7 is a flow diagram of an exemplary process delivering cardiac resynchronization therapy through a LPD in communication with a SICD.

FIG. 7 is a flow diagram of an exemplary method 300 in which CRT such as fusion pacing is delivered to cardiac tissue through LPD 16, in communication with SD 30, in order to address ventricular dyssynchrony present in a patient. Method 300 begins during or after the SD 30 and LPD 16 are implanted into the patient. If the heart 12 is exhibiting ventricular dyssynchrony during the implant procedure, LPD 16 is activated to immediately deliver fusion pacing. Alternatively, if the heart 12 is not exhibiting ventricular dyssynchrony during the implant procedure, one of the SD 30 and LPD 16 determines whether the heart 12 is exhibiting ventricular dyssynchrony and then delivers CRT (i.e. fusion pacing). While method 300 is described as the SD 30 and LPD 16 in a master-slave communication mode, skilled artisans understand that other communication means described herein can be applied. Additionally, method 300 is not limited to the FIG. 1 embodiment in which LPD 16 is affixed to an inner wall of the left ventricle and is wireless communication with SD 30. Other configurations can be used such as, for example, the RV can undergo fusion pacing instead of the LV. Additionally, LPD 16 can be placed on an outer wall of the LV and/or RV.

At block 302, a determination is made as to whether electrical stimuli (e.g. pacing pulses) should be switched to asynchronous pacing of the cardiac tissue. Exemplary cardiac conditions that cause method 300 to switch to asynchronous pacing include an irregular rhythm such as atrial tachycardia (AT), atrial fibrillation (AF), ventricular tachycardia (VT), or ventricular fibrillation (VF). If the condition to switch to asynchronous pacing is met, the YES path continues to block 304. SD 30 generates a command signal to LPD 16, which causes LPD 16 to switch to asynchronous pacing. Asynchronous pacing continues until the irregular rhythm is no longer present in the patient. When the suspend condition terminates (NO path from block 302) the LPD transitions to block 306 in order to evaluate intrinsic electrical conduction and recalculate parameters applied during synchronous pacing.

If the suspend condition is not met such that the patient has a regular rhythm, the NO path continues from block 302 to block 306. At block 306, intrinsic electrical activation of the heart is evaluated using SD 30. For example, a first electrical signal (also referred to as the baseline rhythm or intrinsic rhythm) is sensed from a heart as a subcutaneous ECG through electrodes 34 associated with the SD 30. The baseline rhythm is typically determined at implant; however, the baseline can also be updated during a post-implant visit to a physician's office. Data sampled or extracted from the first signal is stored into memory 72 of the SD 30. Exemplary data from the first electrical signal includes intrinsic electrical activation data (e.g. QRS complex) for the ventricles.

At block 308, electrical activation time or local electrical activity is determined relative to timing of a fiducial, an indicator of a global cardiac event (e.g. timing of activation of a chamber of the heart, timing of pacing of a chamber of the heart, etc.). For example, the fiducial may be the onset of QRS, the peak of QRS (e.g. minimum values, minimum slopes, maximum slopes), zero crossings, threshold crossings, etc. of a near or far-field electrogram (EGM), onset of application of a pacing electrical stimulus, or the like.

After electrocardiogram (ECG) data has been extracted from the first electrical signal for an intrinsic rhythm during a conduction test beat (or without a conduction test beat), the ECG data is filtered with a low pass filter. For instance, the low pass filter could be implemented as a moving average executed in two loops. The number of samples in the moving average could be adjusted to achieve good attenuation at 50 Hz and 60 Hz line frequencies for the sampling rate set, for example, at 256 Hz. The time derivative of the signal dV/dt) can then be calculated. Fiducial points associated with a QRS complex or P-wave can be determined by finding the samples for which the derivative is outside the predetermined boundaries, as described in U.S. Pat. No. 7,941,218 to Sambelashvili, incorporated by reference in its entirety.

The processor 70 of the SD 30 retrieves the data from the first electrical signal (i.e. baseline) from memory 72 and a determination is made by the SD 30 as to the appropriate timing in which electrical stimuli (e.g. pacing pules etc.) are delivered to cardiac tissue at block 310 by the LPD 16. The timing of the delivery of pacing pulses can be predetermined and stored as a lookup table into the memory 72 of the SD 30 and/or the LPD 16. The timing could be also programmable by the user of the system. For example, the timing of pacing by the LPD 16 can be optimized by delivering pacing at a pre-specified interval after the end of a P-wave. The pre-specified interval is either a fixed number or calculated by the SD 30 from widths of the P-wave and paced QRS complex. In one or more embodiments, pre-specified interval fixed number ranges from about 0 ms to about 60 ms and can be typically set at about 30 ms. Alternatively, the timing of pacing by LPD 16 can be optimized by delivering pacing at a pre-specified interval relative to the onset of the QRS complex. The pre-specified fixed number can range from 0 to 60 ms and is typically set at 0 ms. In sum, the LPD 16, in communication with SD 30, is configured to pace relative to fiducial points with pre-specified intervals (e.g. at the detected onset of QRS, 30 ms after the detected end of the P-wave or another suitable rule for timing of pacing). The SD 30 then wirelessly sends a command signal to the LPD 16 to deliver electrical stimuli (e.g. pacing pulses) to the tissue surrounding LPD 16.

At block 312, a determination is made as to whether intrinsic condition of the heart 12 should be re-evaluated. An exemplary re-evaluation condition requires that the heart rhythm is regular and/or a pre-specified time interval has elapsed since the suspend condition ended. The time interval could range from approximately 30 seconds to 24 hours. The time interval could also depend on the daily activity level of the patient, quantified by the activity sensor, so that higher levels of activity correspond to more frequent re-evaluations of intrinsic conduction. For example, periodic conduction tests can be performed to determine whether LPD 16 pacing should be adjusted to maintain AV and VV synchrony. Paced QRS morphology is analyzed by the SD 30 to verify VV synchrony. If the re-evaluation condition is met, then the YES path from block 312 returns to block 306 and the method 300 is continued. For example, when SD 30 re-evaluates the intrinsic conduction, a new baseline signal is recorded and is processed as previously described.

The SD 30 can verify the efficiency and/or efficacy of CRT at block 314. Efficiency of CRT requires that the post-implant or second electrical signal (i.e. current rhythm) be compared to the first electrical signal (i.e. baseline). The second electrical signal is recorded via electrodes 34 on SD 30 and/or electrode 54 on LPD 16 and then stored into memory 72 of the SD 30. Data is extracted from the second electrical signal using techniques known in the art. The processor 70 of the SD 30 retrieves the data from the first electrical signal (i.e. baseline) from memory 72 and compares that data to the data extracted from the second electrical signal (i.e. post-implant signal). Exemplary methods for comparing the two signals for the purpose of optimizing the timing of the delivery of pacing pulses can be found, in U.S. Pat. No. 8,145,308 to Sambelashvili et al., entitled METHOD AND APPARATUS FOR DETERMINING A PARAMETER ASSOCIATED WITH DELIVERY OF THERAPY IN A MEDICAL DEVICE, assigned to the assignee of the present disclosure, incorporated by reference in its entirety. Other exemplary methods that can be usefully applied include template matching disclosed in U.S. Pat. Nos. 6,393,316 B1 and 8,521,268, incorporated by reference in its entirety. Another method employs selected data from each signal for comparison purposes as described in US Patent Application No. 20130053906 A1, which is also incorporated by reference in its entirety.

Figure 8:
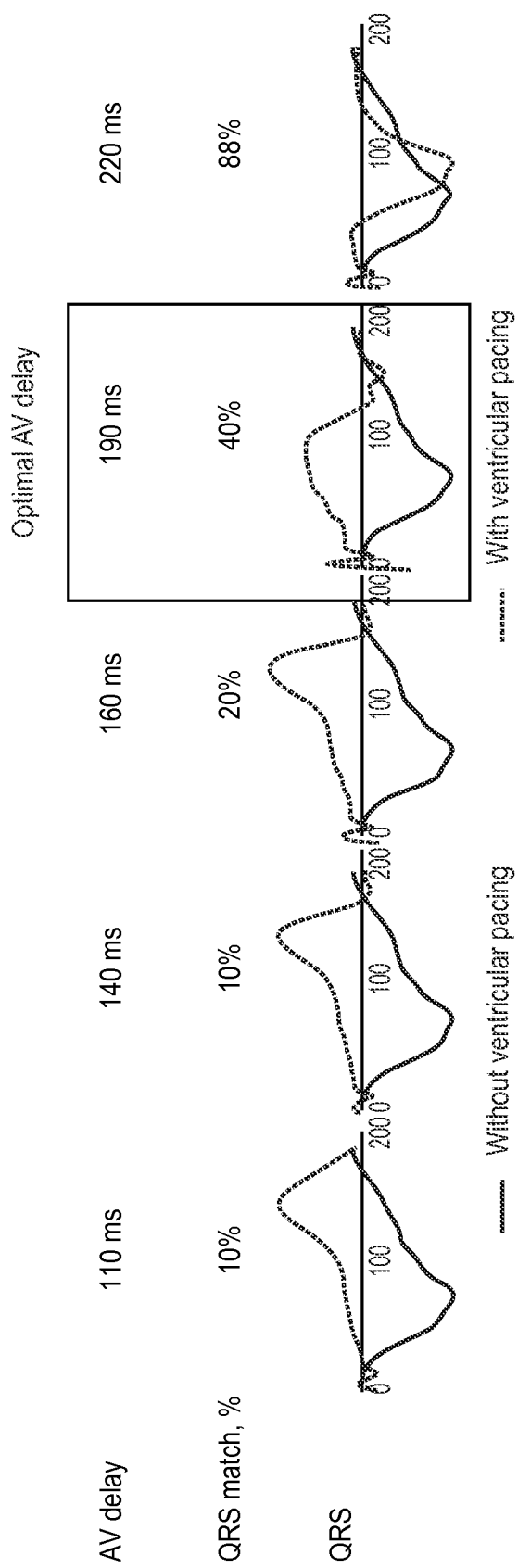
FIG. 8 is a diagram that compares QRS complexes during fusion pacing to QRS complexes that occur during intrinsic rhythm.

FIG. 8 graphically depicts a comparison that was made between a second electrical signal (i.e. rhythm sensed when ventricular pacing is performed) to a heart's baseline or intrinsic rhythm. In this embodiment, the baseline rhythm (i.e. without ventricular pacing) is associated with ventricular dyssynchrony. As applied to FIG. 8, the closer the second electrical signal matches the baseline rhythm (i.e. first electrical signal), the more likely the patient is experiencing ventricular dyssynchrony. In contrast, the greater the difference between the first and second electrical signals, the more likely the patient's ventricles are in synchrony. In particular, fusion pacing is deemed to successfully treat ventricular dyssynchrony when the QRS complexes sensed during pacing are sufficiently different from QRS complexes of the intrinsic rhythm. Wavelet analysis was used to perform the QRS complex comparison, as described in U.S. Pat. No. 6,393,316 to Jeffrey Gillberg et al., incorporated by reference. Wavelet analysis can quantify fusion and optimize timing as described in U.S. Pat. No. 8,145,308, incorporated by reference in its entirety. Additionally, AV intervals can be optimized through U.S. Pat. No. 8,214,041 to Van Gelder et al. incorporated by reference in its entirety.

The dashed line is the electrical signal sensed from the ventricle without ventricular pacing (i.e. baseline rhythm) while the solid line is associated an electrical signal sensed from the ventricle during ventricular pacing. The window encompasses an optimal AV delay of 190 ms in which the QRS complexes reveal a 40% QRS match. From FIG. 8, fusion pacing has corrected the ventricular dyssynchrony by setting the AV delay to 190 ms. If the QRS complexes from the baseline rhythm more closely match the QRS complex from ventricular pacing, then fusion pacing is not effective.

For instance, effective fusion can be achieved when to the match score between the paced and intrinsic QRS complexes is less than 70%. The target range for the score can be 40-70%, otherwise the resynchronization can be classified as ineffective.

If fusion pacing was ineffective, the NO path from block 314 continues to block 316 in which another pre-specified interval is selected. Another pre-specified interval can be selected from a lookup table, pre-specified by the user, or adjusted by a rule. For instance, the pre-specified interval can be decremented or incremented by 20 ms for a new evaluation of the resynchronization effectiveness. Thereafter, the process flow continues to block 310.

While method 300 is described relative to LPD 16 placed in the left ventricle, skilled artisans appreciate that the present disclosure can be applied to many different embodiments in which SD 30 is used in combination with LPD 16. For example, the LPD can be implanted within a chamber of the heart or substernally/retrosternally, as described in U.S. provisional patent application Ser. No. 61/819,946 filed May 6, 2013 and entitled "IMPLANTABLE MEDICAL DEVICE SYSTEM HAVING IMPLANTABLE CARDIAC DEFIBRILLATOR SYSTEM AND SUBSTERNAL LEADLESS PACING DEVICE", incorporated by reference in its entirety, U.S. provisional patent application Ser. No. 61/820,024 filed May 6, 2013 and entitled "ANCHORING AN IMPLANTABLE MEDICAL DEVICE WITHIN A SUBSTERNAL SPACE, and U.S. provisional patent application Ser. No. 61/820,014 filed May 6, 2013 and entitled "SYSTEMS AND METHODS FOR IMPLANTING A MEDICAL ELECTRICAL LEAD WITHIN A SUBSTERNAL SPACE", all of which are incorporated by reference herein. The SD is configured to deliver shocks to the patient without any leads implanted within the vasculature and/or heart of the patient.

Figure 9A:
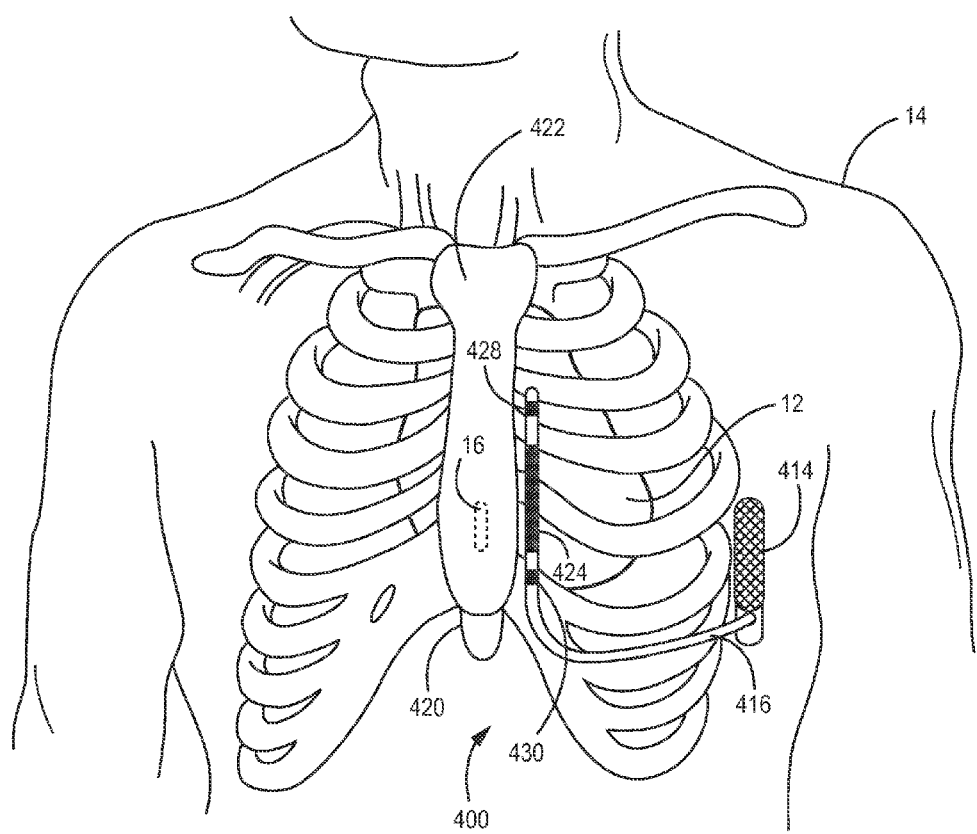
FIGS. 9A-C are conceptual diagrams of a patient implanted with an exemplary substernal/retrosternal implantable cardiac system.
Figure 9B:
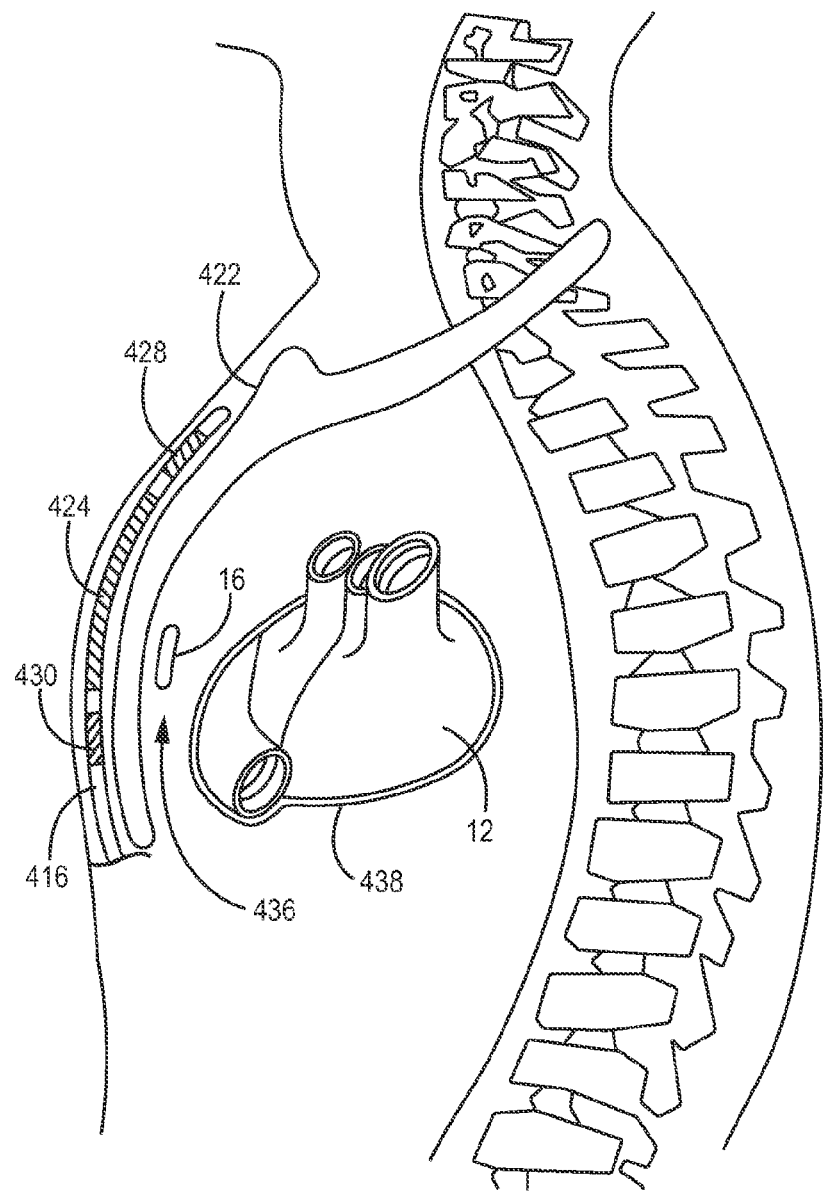
Figure 9C:
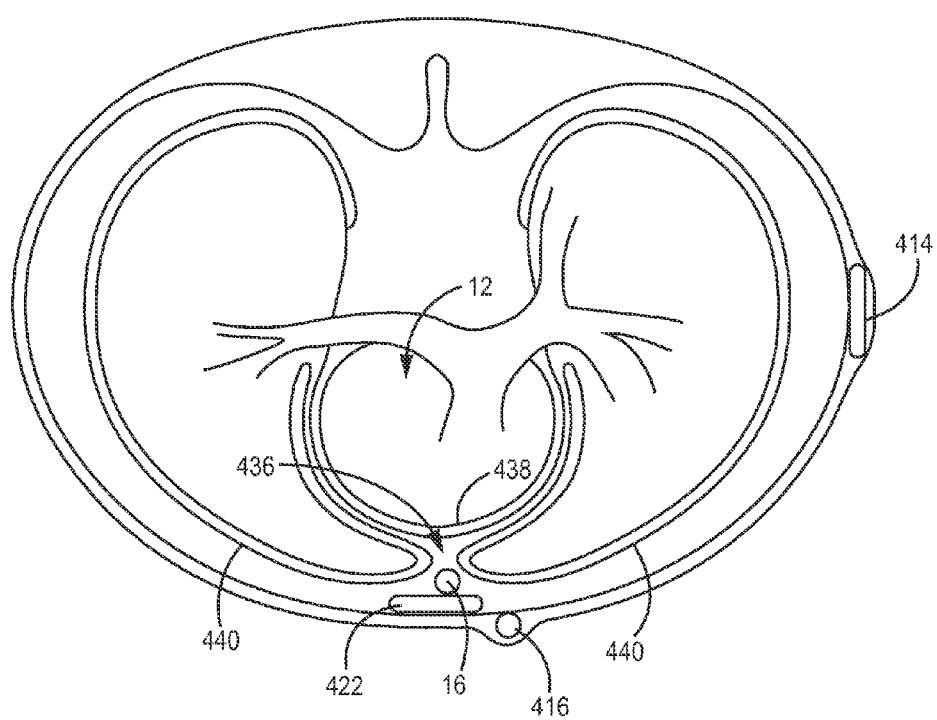

FIGS. 9A-C are conceptual diagrams of a patient 14 implanted with an exemplary implantable cardiac system 400 that includes a substernal/retrosternal LPD 16 in order to deliver CRT (e.g. fusion pacing, biventricular pacing or adaptive CRT (i.e. switching between biventricular pacing and fusion pacing). Implantable cardiac system 400 can implement method 300 as described herein. FIG. 9A is a front view of patient 14 implanted with implantable cardiac system 400. FIG. 9B is a side view patient 14 with implantable cardiac system 400. FIG. 9C is a transverse view of patient 14 with implantable cardiac system 400.

Implantable cardiac system 400 includes an implantable medical device 414 such as an implantable cardiac defibrillator (ICD) or pacemaker connected to a defibrillation lead 416. In the example illustrated in FIGS. 9A-C, IMD 414 is implanted subcutaneously on the left midaxiallary of patient 14. IMD 414 may, however, be implanted at other subcutaneous locations on patient 14 as described herein.

Defibrillation lead 416 includes a proximal end that is connected to IMD 414 and a distal end that includes one or more electrodes. Defibrillation lead 416 extends subcutaneously from IMD 414 toward xiphoid process 20. At a location near xiphoid process 20 defibrillation lead 416 bends or turns and extends subcutaneously superiorily, substantially parallel to sternum 422. The distal end of defibrillation lead 416 may be positioned near the second or third rib of patient 14. However, the distal end of defibrillation lead 416 may be positioned further superior or inferior depending on the location of IMD 414 and other factors. Although illustrated as being offset laterally from and extending substantially parallel to sternum 422 in the example of FIGS. 9A-C, defibrillation lead 416 may be implanted over sternum 422, offset from sternum 422, but not parallel to sternum 422 (e.g., angled lateral from sternum 422 at either the proximal or distal end).

Defibrillation lead 416 includes a defibrillation electrode 424, which may be an elongated coil electrode, toward the distal end of defibrillation lead 416. Defibrillation lead 416 is placed such that a therapy vector between defibrillation electrode 424 and a housing or can electrode of IMD 414 is substantially across the ventricle of heart 12.

Defibrillation lead 416 may also include sensing and/or pacing electrodes 428 and 430 located toward the distal end of defibrillation lead 416. In the example illustrated in FIGS. 9A-C, sensing electrode 428 and 430 are separated from one another by defibrillation electrode 424. IMD 414 may sense electrical activity of heart 26 via a combination of sensing vectors that include combinations of electrodes 428 and 430 and the housing or can electrode of IMD 414. For example, IMD 414 may obtain electrical signals sensed using a sensing vector between electrodes 428 and 430, obtain electrical signals sensed using a sensing vector between electrode 428 and the conductive housing or can electrode of IMD 414, obtain electrical signals sensed using a sensing vector between electrode 430 and the conductive housing or can electrode of IMD 414, or a combination thereof. In some instances, IMD 414 may even sense cardiac electrical signals using a sensing vector that includes defibrillation electrode 424.

ICD 414 may analyze the sensed electrical signals from one or more of the sensing vectors of defibrillation lead 416 to detect ventricular dyssynchrony and/or other cardiac conditions (e.g. tachycardia, fibrillation). In response to detecting the ventricular dyssynchrony, IMD 414 may communicate with LPD 16 to initiate fusion pacing or biventricular pacing in an attempt to terminate the ventricular dyssynchrony. The means of communication between LPD 16 and IMD 414 is the same or similar as that which is described herein.

LPD 16 is implanted substernally/retrosternally and communicatively coupled to IMD device 414. LPD 16 and IMD device 414 may, for example, both include a communication module via which the devices exchange wireless communications. LPD 16 and IMD device 414 may, for example, be coupled via inductive coupling, RF coupling, tissue conductance communication, or other wireless communication mechanism.

As indicated above, LPD 16 is implanted substernally/retrosternally, e.g., in the substernal/retrosternal space underneath the sternum but not within the pericardial space or the pleural space. In one example, LPD 16 may be placed in the mediastinum 436 and, more particularly, in the anterior mediastinum. The anterior mediastinum is bounded laterally by pleurae 440, posteriorly by pericardium 438, and anteriorly by sternum 22. LPD 16 may be implanted within the mediastinum such that the one or more electrodes of LPD 16 are located over a cardiac silhouette of the ventricle as observed via fluoroscopy. In the example illustrated in FIGS. 9A-C, LPD 16 is located substantially centered under sternum 422. In other instances, however, LPD 16 may be implanted such that it is offset laterally from the center of sternum.

Although described herein as being implanted in the substernal/retrosternal space, the mediastinum, or the anterior mediastinum, LPD 16 may be implanted in other extra-pericardial locations. In this disclosure, the term "extra-pericardial locations" refers to locations in the region around, but not in contact with, the outer heart surface. The region defined as the extra-pericardial includes the gap, tissue, bone, or other anatomical features around the perimeter of, and adjacent to, but not in contact with the pericardium. These may include the superior mediastinum, middle mediastinum, posterior mediastinum, in the sub-xiphoid or inferior xiphoid area, near the apex of the heart, or other location not in intimate contact with the heart and not subcutaneous.

LPD 16 is configured to include a housing 31, electrodes 432 and 434 coupled to the housing or formed by the housing, and a fixation mechanism (e.g., tines 35 of FIG. 3) to attach LPD 16 at a desired substernal/retrosternal location. LPD 16 may have other fixation mechanisms besides tines 35.

LPD 16 may sense electrical activity of heart 12 via electrodes 432 and 434 and provide pacing pulses to heart 12 via electrodes 432 and 434. The pacing pulses provided to heart 12 may be responsive to sensed electrical signals of the heart sensed either via electrodes 432 and 434 of LPD 16 or sensed via one or more electrode combinations of defibrillation lead 16. LPD 16 may generate and deliver pacing pulses with any of a number of amplitudes and pulse widths to capture heart 12.

LPD 16 may also analyze the sensed electrical signals from one or more of the sensing vectors of LPD 16 and/or from the IMD to detect ventricular dyssnchrony. LPD 16 may not deliver CRT therapy (e.g. fusion pacing or biventricular pacing) until LPD 16 receives a communication from IMD 414 indicating detection of ventricular dyssnchrony by IMD 414.

The configuration described above in FIGS. 9A-9C is directed to providing ventricular pacing via LPD 16. However, other LPDs 16 may be positioned further superior or inferior. In some instances, more than one LPD 16 may be utilized for dual chamber pacing, e.g., with one LPD 16 providing atrial pacing and the other LPD 16 providing ventricle pacing. Alternatively, LPD 16 may be positioned over the ventricle and include a small tether extending up to the atrium with an electrode on the tether. LPD 16 could sense and/or pace via the electrode on the tether. As another alternative, LPD 16 could be elongated to serve this purpose under the sternum, so that there is one or more electrodes on the housing that senses/paces one of the heart chambers and one or more electrodes on the housing that senses/paces ventricle. In yet further embodiments, LPD 16 may be used in combination with a pacing lead implanted substernally to provide dual chamber pacing.

ICD 414 may include a housing that forms a hermetic seal that protects components of IMD 414. The housing of IMD 414 may be formed of a conductive material, such as titanium. IMD 414 may also include a connector assembly (also referred to as a connector block or header) that includes electrical feedthroughs through which electrical connections are made between conductors within the lead 416 and electronic components included within the housing. As will be described in further detail herein, housing may house one or more processors, memories, transmitters, receivers, sensors, sensing circuitry, therapy circuitry and other appropriate components. The housing 434 is configured to be implanted in a patient, such as patient 414.

Lead 416 includes a lead body that includes electrodes 424, 428 and 430 located near the distal lead end or elsewhere along the length of the lead body. The lead bodies of lead 416 also contain one or more elongated electrical conductors (not illustrated) that extend through the lead body from the connector assembly of IMD 414 provided at a proximal lead end to one or more electrodes of lead 416. The lead bodies of lead 416 may be formed from a non-conductive material, including silicone, polyurethane, fluoropolymers, mixtures thereof, and other appropriate materials, and shaped to form one or more lumens within which the one or more conductors extend. However, the techniques are not limited to such constructions.

The one or more elongated electrical conductors contained within the lead bodies of lead 16 may engage with respective ones of electrodes 424, 428, and 430. In one example, each of electrodes 424, 428, and 430 is electrically coupled to a respective conductor within its associated lead body. The respective conductors may electrically couple to circuitry, such as a therapy module or a sensing module, of IMD 414 via connections in connector assembly, including associated feedthroughs. The electrical conductors transmit therapy from a therapy module within IMD 414 to one or more of electrodes 424, 428, and 430 and transmit sensed electrical signals from one or more of electrodes 424, 428, and 430 to the sensing module within IMD 414.

The examples illustrated in FIGS. 9A-C are exemplary in nature and should not be considered limiting of the techniques described in this disclosure. In other examples, IMD 414 and defibrillation lead 416 may be implanted at other locations. For example, IMD 414 may be implanted in a subcutaneous pocket in the right chest. In this example, defibrillation lead 416 may be extend subcutaneously from the device toward the manubrium of the sternum and bend or turn and extend subcutaneously inferiorly from the manubrium of the sternum, substantially parallel with the sternum.

In the example illustrated in FIG. 9, system 400 includes an IMD system that provides, but the techniques may be applicable to other cardiac systems, including cardiac resynchronization therapy defibrillator (CRT-D) systems, cardioverter systems, or combinations thereof.

Skilled artisans appreciate that the substernal/retrosternal IMD system 400 can be configured to deliver biventricular pacing to synchronize the ventricles with each other. Biventricular pacing consists of pacing the right ventricle (RV) with a RV electrode and a left ventricle (LV) with a LV electrode. Electrodes 428 and 430 can be configured to deliver pacing pulse to the LV. The LV and/or RV is paced by separate electrodes (e.g. a LPD 16 connected through tines to the inner or outer surface of the wall of the RV, an electrode on a medical electrical lead etc.). In one or more embodiments, IMD system 400 can be configured to automatically switch between biventricular pacing and fusion pacing. Typically, the primary goal is to ensure the ventricles are synchronized with each other. Monoventricular pacing or fusion pacing is preferred over biventricular pacing provided the ventricles achieve synchrony. Skilled artisans appreciate that a patient's heart may require adaptive CRT in which biventricular pacing is required during one period of time (e.g. 1 hour, day, week etc.) and at another time, fusion pacing may be all that is necessary to return the ventricles to synchrony. Typically, fusion pacing involves pacing the LV; however, there are conditions in which the RV is solely paced.

Adaptive LV pacing leverages intrinsic RV conduction by pre-pacing the LV to synchronise with intrinsic RV activation. The timing of the LV pace is automatically adjusted based on the atrial to intrinsic QRS interval measurement (AV interval). One or more embodiments can set the LV pace to occur at about 70% of the intrinsic AV interval, but at least 40 ms prior to the intrinsic QRS.

One or more other embodiments can set the LV pace to occur at about a moderately lengthened QRS. For example, if the QRS width exceeds 120 ms, but does not exceed 160 ms, then LV pacing with fusion is selected. Otherwise, if the QRS width is greater than 160 ms, then BiV pacing is selected. Implementing a moderately lengthened QRS threshold may benefit heart failure patients. Efficacies of LV only pacing or biventricular pacing may be predicted by the moderately lengthened QRS duration. An exemplary moderately lengthened QRS corresponds to QRS width in the range of 130-150 ms. LV pacing for moderately lengthened QRS can achieve superior results compared to echocardiographic optimization. In one or more embodiments, the intrinsic AV conduction is automatically evaluated. In one or more other embodiments, the IMD (e.g. ICD etc.), LPD and/or SD automatically evaluates intrinsic ventricular conduction based upon QRS duration from the far-field EGM or right ventricular sense to left ventricular sense (RVs-LVs) interval from the IMD sensing markers is automatically evaluated by the IMD or SD. U.S. Pat. No. 4,374,382 issued to Markowitz et al. describes IMD sensing markers, which is incorporated by reference in its entirety. Based on the results, fusion pacing (i.e. LV only pacing or RV only pacing) or biventricular pacing. RVs-LVs interval not exceeding 150 ms could correspond to LV only pacing, whereas >150 ms could switch the algorithm to biventricular pacing. In one or more other embodiments, RVs-LVs interval not exceeding 80 ms corresponds to fusion pacing while greater than 80 ms switches to biventricular pacing. Typically, RVs-LVs are shorter than the corresponding QRS width. Therefore, it takes about 40 ms to sense the onset of QRS in the RV and the final portion of the QRS in the LV is also sensed prior to the QRS end.

In one or more other embodiments, the IMD tracks the moderately lengthened QRS over time and then relies on trend data to switch between biventricular pacing and fusion pacing. For example, assume that the moderately lengthened QRS is 120 ms, 125 ms, 130 ms, 135 m, 140 ms, and 145 ms, respectively for 6 consecutive weeks. The increasing trend could trigger the switch to biventricular pacing before the threshold is met for switching to biventricular pacing.

In another embodiment, the SD could send a control signal to the LPD to initiate CRT. The LPD could sense a cardiac signal (i.e. a second electrical signal) from the heart of the patient. Based on the cardiac signal, the LPD could determine whether to deliver CRT to the heart from the LPD. For example, the LPD, based on the second electrical signal, could determine that CRT is not necessary. The LPD could consider whether sensed data meets a pre-specified threshold. For instance if the QRS width does not exceed 120 ms, the LPD may withhold the delivery of CRT therapy (e.g. the LPD could then signal the SD that CRT should not be delivered based upon the cardiac signal. The SD can be configured to perform a more detailed analysis in which at least one or more parameters (such as at least two parameters) are evaluated. The SD could then send another command signal that confirms, denies or overrides the LPD.

In another embodiment, the LPD could sense a cardiac signal that indicates a switch between fusion pacing to biventricular pacing should occur and would signal the SD. The SD could be configured to send an override signal to the LPD unless certain conditions are met.

In yet another embodiment, the LPD could determine that biventricular pacing is required over fusion pacing in contravention to the SD communication. In one embodiment, the LPD would deliver biventricular pacing. In one or more other embodiments, the LPD could determine that fusion pacing is required over biventricular pacing in contravention to the SD communication. In this scenario, the LPD could deliver fusion pacing.

In another embodiment, the SD transmits a control signal to the LPD to initiate CRT. The LPD senses a cardiac signal (i.e. a second electrical signal) from the heart of the patient. Based on the cardiac signal, the LPD could determine whether to deliver CRT or the type of CRT to deliver to the heart from the LPD. In one or more embodiments, the LPD, based on the second electrical signal, could initially determine that CRT is not necessary. The initial determination by the LPD could use very simplified tests such as a threshold of one or more parameters. In one or more embodiments, the SD could perform a more detailed analysis as to whether CRT should be delivered. Using the sensed data from the LPD and/or SD, the SD could generate another signal to the LPD that either confirms, denies or overrides the LPDs initial determination.

In another embodiment, the LPD could sense a cardiac signal that indicates a switch should occur between fusion pacing to biventricular pacing. Determining whether to switch between fusion pacing and biventricular pacing could be determined based upon one or more parameters (e.g. moderately lengthened QRS, etc.). The LPD could be configured to either automatically switch between fusion pacing and biventricular pacing or to wait until the SD confirms or denies switching between the CRT pacing mode (i.e. fusion pacing and biventricular pacing). The SD could be configured to send a confirmatory signal or a signal denying the LPD switching the pacing mode.

In yet another embodiment, the LPD could determine that biventricular pacing is required over fusion pacing in contravention to the SD communication. In one embodiment, the LPD would deliver biventricular pacing. In one or more other embodiments, the LPD could determine that fusion pacing is required over biventricular pacing in contravention to the SD communication. In this scenario, the LPD could deliver fusion pacing.

In one or more other embodiments, SD is implanted into a patient's heart. For example, the SD could be a conventional ICD or a SD described herein). Electrical signals are then sensed which includes moderately lengthened QRS duration data from the patient's heart. A determination is made as to whether cardiac resynchronization pacing therapy (CRT pacing) is appropriate based upon the moderately lengthened QRS duration in the sensed electrical signals. The CRT pacing pulses are delivered to the heart using electrodes. In one or more embodiments, the SD can switch between fusion pacing and biventricular pacing based upon data (e.g. moderately lengthened QRS, etc.) sensed from the heart.

There are many different embodiments that may be implemented with the methods described herein. One or more LPDs carrying one or more electrodes may be implanted within various chambers of the heart of the patient or otherwise in close proximity of the cardiac muscle. At these locations, an LPD may sense ECG signals with high signal-to-noise ratios to detect arrhythmias. In addition, an LPD may provide cardiac pacing at the location of the implanted LPD. In some examples, one or both of SD and LPD may share detected signals or physiological information (e.g., R-R intervals, electrogram morphology measurements, and/or electrocardiograms or electrograms) such that the device receiving such information can determine a condition of patient 14 (e.g., determine whether or not patient 14 is experiencing an arrhythmia and or lack of synchrony between ventricles). Communication between an LPD and a SICD is described in U.S. patent application Ser. No. 13/756,085, filed on Jan. 31, 2013, incorporated herein in its entirety.

In some examples, communication between the SICD and an LPD may be used to initiate therapy and/or confirm that therapy should be delivered. The SICD may also transmit a communication message to the LPD instructing the LPD to change one or more parameters that define the CRT therapy. In this one-way communication example the SICD may be configured to transmit communications to the LPD and the LPD may be configured to receive the communication from the SICD. Alternatively, one-way communication may be established such that the LPD may be configured to transmit communications to the SICD (e.g., communication from LPD 16). In other examples, two-way communication may allow confirmation of a detected of a cardiac condition (e.g. ventricular dyssynchrony, tachyarrhythmia, bradycardia etc.) prior to delivery of any therapy. Communication between the SD and the LPD is described in greater details in U.S. patent application Ser. No. 13/756,085 filed May 26, 2013 and entitled "SYSTEMS AND METHODS FOR LEADLESS PACING AND SHOCK THERAPY", incorporated by reference in its entirety.

The systems and techniques described herein may be generally related to cooperative monitoring of a patient and/or therapy delivery to the patient using multiple implanted devices such as an SD and an LPD. In one example, the SD and LPD may detect the functions of each other and/or communicate to coordinate monitoring and therapy such as CRT. However, the SD and LPD may coordinate other monitoring and therapy features. For example, using the communication techniques described herein, prior to either the SD or LPD delivering therapy, sensed data from both devices may be used to determine if the therapy should be delivered. In some examples, the SD or the LPD may be configured to override the other device in situations in which there is a discrepancy between whether or not physiological condition is occurring. In any case, the SD and LPD may be configured to function together to monitor and/or provide therapy to patient 14.

The techniques described herein may provide for a SD and LPD to operate cooperatively within a patient to monitor the heart for arrhythmias and deliver appropriate therapy to treat any detected arrhythmias. For example, an SD and LPD may detect ventricular dyssynchrony and deliver CRT. Wireless communication between the SD implanted external of the rib cage and one or more LPDs implanted within the heart may provide various ECG or EGM sensing vectors.

The disclosure also contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

In addition, it should be noted that system 400 may not be limited to treatment of a human patient. In alternative examples, system 400 may be implemented in non-human patients, e.g., primates, canines, equines, pigs, and felines. These other animals may undergo clinical or research therapies that may benefit from the subject matter of this disclosure.

The techniques described in this disclosure, including those attributed to SD 30, LPD 16, programmer 20, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices, such as between SD 30, LPD 16 and/or programmer 20. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache). Various examples have been described for detecting arrhythmias and delivering anti-tachycardia therapy via a subcutaneous implantable cardioverter defibrillator and/or a leadless pacing device. Any combination of the described operations or functions is contemplated. These and other examples are within the scope of the following claims.

What is claimed is:

1. A method of using a subcutaneous device (SD) in a patient and a leadless pacing device (LPD) in the patient's heart, the method comprising:
   sensing electrical signals which includes moderately lengthened QRS data from the patient's heart using the SD;

employing the SD to determine whether cardiac resynchronization pacing therapy (CRT pacing) is appropriate based upon the QRS duration in the sensed electrical signals;

employing the SD to determine timing of CRT pacing pulses for delivery to cardiac tissue through the LPD and sending signals indicative thereof to the LPD responsive to the sent indicative signals;

delivering the CRT pacing pulses to the heart using the LPD;

thereafter sensing subsequent electrical signals from the patient's heart using the SD; and determining, by the SD based on the subsequent electrical signals, whether the CRT pacing by the LPD provided efficacious resynchronization and whether the delivery and timing of subsequent CRT pacing pulses should be modified.

2. A method of claim of 1 wherein the moderately lengthened QRS corresponds to a QRS width in a range of 120-160 ms.

3. A method of claim 1 further comprising:
evaluating intrinsic ventricular conduction based upon the moderately lengthened QRS duration from a far-field electrogram (EGM).

4. A method of claim 1 further comprising:
evaluating an RVs-LVs interval from sensing markers is automatically evaluated by the LPD or the SD.

5. A method of claim 4 wherein the RVs-LVs interval not exceeding 80 ms corresponds to fusion pacing while greater than 80 ms switches to biventricular pacing.

6. A method of claim 1 wherein the SD generates a signal to the LPD to switch to another CRT pacing.

7. A method of claim 6 further comprising switching from the CRT pacing to another CRT pacing.

8. A method of claim 7 wherein the SD generates a signal to the LPD to cause switching from CRT pacing to another CRT pacing.

9. A method of claim 8 wherein the CRT pacing and the another CRT pacing being one of fusion pacing and biventricular pacing.

10. A method of claim 9 further comprising:
sensing another electrical signal from the cardiac tissue via the LPD indicating fusion pacing being appropriate pacing to deliver to cardiac tissue; and
generating a signal to the SD from the LPD communicating fusion pacing data.

11. A method of claim 10 further comprising:
processing the another electrical signal; and
determining by the SD whether the another electrical signal indicates that a switch to another CRT pacing should occur.

12. A method of claim 7 wherein the SD generates a signal to the LPD confirming switching to another CRT pacing.

13. A method of claim 12 wherein the CRT pacing being one of fusion pacing and biventricular pacing.

14. A method of claim 12 further comprising:
generating an overriding signal from the SD to the LPD.

15. A method of claim 14 wherein the SD generates a signal to the LPD confirming switching to another CRT pacing.

16. A method of claim 1 further comprising:
sensing electrical signals from a substernally placed lead extending from the SD.

17. A method comprising:
sensing electrical signals which includes moderately lengthened QRS duration data from the patient's heart using a subcutaneous device;
determining whether cardiac resynchronization pacing therapy (CRT pacing) is appropriate based upon the moderately lengthened QRS duration in the sensed electrical signals; and
delivering the CRT pacing pulses to the heart using a leadless pacing device (LPD).

18. A method of claim of 17 wherein the moderately lengthened QRS corresponds to a QRS width in the range of 120-160 ms.

19. A method of claim 17 further comprising:
evaluating intrinsic ventricular conduction based upon the moderately lengthened QRS duration from a far-field EGM.

20. A method of claim 17 further comprising:
evaluating an RVs-LVs interval from sensing markers is automatically evaluated by the LPD or the SD.

21. A method of claim 20 wherein the RVs-LVs interval not exceeding 80 ms corresponds to fusion pacing while greater than 80 ms switches to biventricular pacing.

22. A system for cardiac pacing comprising:
a subcutaneous device (SD) in a patient;
a leadless pacing device (LPD) in the patient's heart;
sensing means for sensing electrical signals which includes moderately lengthened QRS data from the patient's heart using the SD;
processing means for employing the SD to determine whether cardiac resynchronization pacing therapy (CRT pacing) is appropriate based upon the QRS duration in the sensed electrical signals;
processing means for employing the SD to determine timing of CRT pacing pulses for delivery to cardiac tissue through the LPD and sending signals indicative thereof to the LPD responsive to the sent indicative signals;
delivering means for delivering the CRT pacing pulses to the heart using the LPD;
thereafter sensing means for sensing subsequent electrical signals from the patient's heart using the SD; and
processing means for determining, by the SD based on the subsequent electrical signals, whether the CRT pacing by the LPD provided efficacious resynchronization and whether the delivery and timing of subsequent CRT pacing pulses should be modified.

23. A system of claim of 22 wherein the moderately lengthened QRS corresponds to a QRS width in the range of 120-160 ms.

24. A system of claim 22 further comprising:
evaluating intrinsic ventricular conduction based upon the moderately lengthened QRS duration from a far-field EGM.

25. A system of claim 22 further comprising:
evaluating an RVs-LVs interval from sensing markers is automatically evaluated by the LPD or the SD.

26. A system of claim 25 wherein the RVs-LVs interval not exceeding 80 ms corresponds to fusion pacing while greater than 80 ms switches to biventricular pacing.

* * * * *